(12) United States Patent
Weibel et al.

(10) Patent No.: US 9,050,593 B2
(45) Date of Patent: Jun. 9, 2015

(54) SELF-LOADING MICROFLUIDIC DEVICE AND METHODS OF USE

(75) Inventors: Douglas Weibel, Madison, WI (US); Nathaniel James Cira, Cedarburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 120 days.

(21) Appl. No.: 13/303,982

(22) Filed: Nov. 23, 2011

(65) Prior Publication Data

US 2013/0130232 A1    May 23, 2013

(51) Int. Cl.
*B01L 3/00*         (2006.01)
*G01N 33/543*       (2006.01)

(52) U.S. Cl.
CPC ...... *B01L 3/5027* (2013.01); *Y10T 436/143333* (2015.01); *Y10T 436/25* (2015.01); *G01N 33/54386* (2013.01); *B01L 3/502707* (2013.01); *B01L 2200/16* (2013.01); *B01L 2300/0816* (2013.01); *B01L 2300/0864* (2013.01); *B01L 2300/0887* (2013.01); *B01L 2400/0406* (2013.01); *B01L 2400/049* (2013.01); *B01L 3/50273* (2013.01)

(58) Field of Classification Search
None
See application file for complete search history.

(56) References Cited

U.S. PATENT DOCUMENTS

| | | | |
|---|---|---|---|
| 5,942,443 A | 8/1999 | Parce et al. | |
| 7,150,999 B1 | 12/2006 | Shuck | |
| 2002/0042125 A1* | 4/2002 | Petersen et al. | 435/287.2 |
| 2002/0142618 A1* | 10/2002 | Parce et al. | 438/751 |
| 2006/0205085 A1* | 9/2006 | Handique et al. | 436/177 |
| 2007/0264629 A1* | 11/2007 | Holmes et al. | 435/5 |

OTHER PUBLICATIONS

Luo et al., A Fast Cell Loading and High-Throughput Microfluidic System for Long-Term Cell Culture in Zero-Flow Environments, Biotechnology and Bioengineering, vol. 101, No. 1, Sep. 1, 2008.*
Hosokawa et al., DNA Detection on a Power-free Microchip with Laminar Flow-assisted Dendritic Amplification, Analytical Sciences, vol. 26, pp. 1053-1057, Published Oct. 10, 2010.*
Beebe, D.J., et al., "Physics and Applications of Microfluidics in Biology," Annu. Rev. Biomed. Eng. 4:261-286 (2002).
Dimov, I.K., et al., "Stand-alone self-powered integrated microfluidic blood analysis system (SIMBAS)," Lab Chip 11:845-850 (2011).
Hosokawa, K., et al., "Power-free poly(dimethylsiloxane) microfluidic devices for gold nanoparticle-based DNA analysis," Lab Chip 4:181-185 (2004).
Hosokawa, K, et al., "Power-free sequential injection for microchip immunoassay toward point-of-care testing," Lab Chip 6:236-241 (2006).
Liang, D.Y., et al., "Systematic characterization of degas-driven flow for poly(dimethylsiloxane) microfluidic devices," Biomicrofluidics 5:24108-1-24108-16 (2011).

* cited by examiner

*Primary Examiner* — Melanie Y Brown
*Assistant Examiner* — Rebecca Martinez
(74) *Attorney, Agent, or Firm* — Armstrong Teasdale LLP

(57) ABSTRACT

Microfluidic devices and methods for conducting chemical assays and biological assays using microfluidic devices are disclosed. The microfluidic devices do not require external connections, tethers, tubing, valves and actuators. The microfluidic devices are useful in methods for analyzing a wide variety of chemical and biological assays such as, for example, molecule-molecule interactions, enzyme-substrate interactions, molecule identification, minimum inhibitory concentrations, therapeutically effective amounts, and toxic amounts.

5 Claims, 18 Drawing Sheets

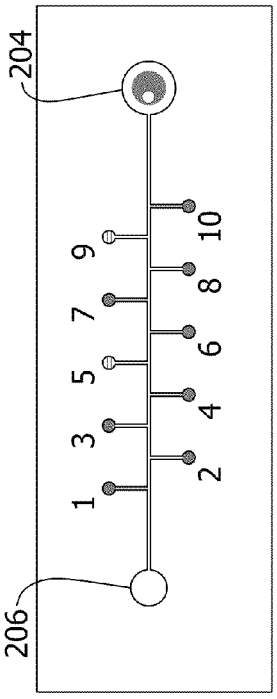
FIG. 29A
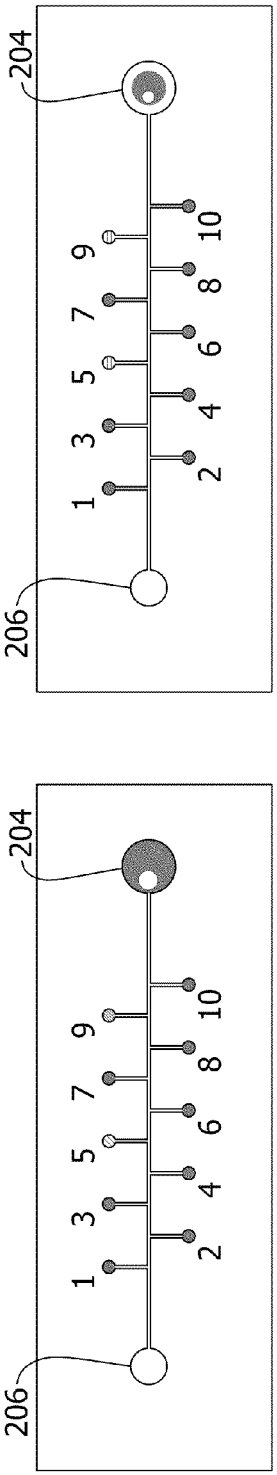
FIG. 29B
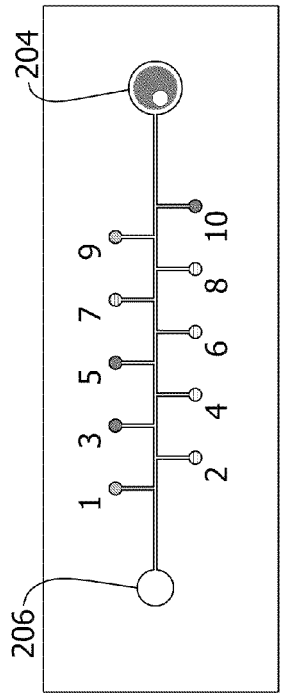
FIG. 29C
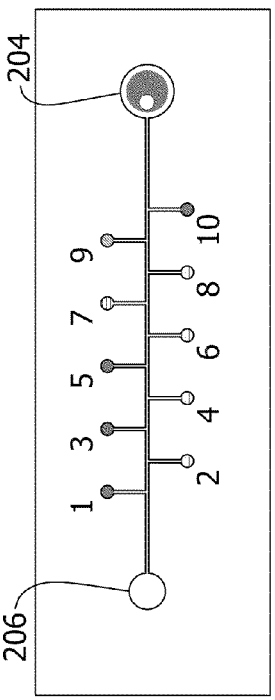
FIG. 29D
FIG. 29E
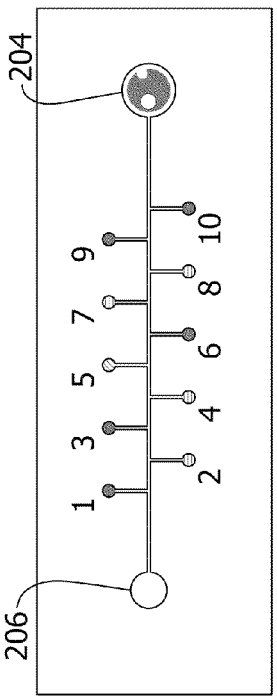
FIG. 29F

SELF-LOADING MICROFLUIDIC DEVICE AND METHODS OF USE

BACKGROUND OF THE DISCLOSURE

The present disclosure relates generally to microfluidic technology. More particularly, the present disclosure relates to self-loading microfluidic devices. The present disclosure further relates to methods of using the self-loading microfluidic devices for chemical assays and biological assays.

The search for new therapeutic agents involves rapidly screening test compounds in chemical assays and biological assays to identify lead compounds for further development. Once lead compounds are identified, additional screening may be needed to identify therapeutically effective amounts and toxicity levels. Screening therapeutic agents is important for patient treatment and for preventing the prescription of ineffective pharmaceuticals. For example, determining the minimum inhibitory concentration (MIC) of antibiotics against bacteria is important for preventing the prescription of ineffective antibiotics that may lead to the spread of antibiotic-resistant strains of bacteria. The minimum inhibitory concentration (MIC) of a compound is generally defined as the lowest dose that inhibits the growth of a cell during a set time interval. Determining the MIC for microbes is particularly important because of the increase in antibiotic-resistant bacteria and the decline in the discovery rate of new antibiotics.

Determining therapeutically effective concentrations including, for example, the MIC of antibiotics against bacteria is generally performed using diffusion or dilution methods. In diffusion methods to determine the MIC of microbes, for example, a hydrophilic strip or disc is infused with antibiotic and placed in contact with the surface of an agar plate upon which a microbe is growing. The antibiotic diffuses radially through the agar gel and forms a concentration gradient that inhibits microbial growth close to the strip or disc. The formation of a visual 'zone of inhibition' in this assay enables the estimation of the MIC. Diffusion-based assays are technically simple to perform, however they have several disadvantages. For example, the results of the assays must be standardized to the specific characteristics of the agar growth media, which strongly influence diffusion of the antibiotics. Additionally, the analysis of these assays is subjective and variable.

Dilution methods to determine the MIC of microbes, for example, involves inoculating microbes into a series of separate culture tubes or onto separate agar plates containing nutrient media and a two-fold serial dilution of an antimicrobial agent. The Clinical Laboratory and Standards Institute (CLSI) in the United States and by similar institutions in other countries publish guidelines for dilution-based methods for determining MIC values. The MIC is determined by identifying the lowest concentration of antibiotic that inhibits microbial growth, and is typically measured by visual inspection. These assays are well characterized and provide a more quantitative readout than diffusion methods, however, they are generally more labor intensive. The use of a liquid handling robot to prepare dilution series in multiwell plates can reduce the time and labor involved, however these instruments are expensive and not widely available in laboratories.

Screening may also be used to conduct other chemical assays and biological assays such as, for example, analyzing cellular samples, performing and analyzing enzymatic reactions, identifying binding partners, and detecting target molecules. Immunoassays, for example, are commonly used for molecular recognition based on the specific interaction between an antibody and its antigen. Strip immunoassays have been successful for point-of-care clinical diagnosis because of its ease of use and rapid and sensitive format. However, the strip immunoassay may not be applicable for all immunoassays, and thus, many immunoassays are conducted using microtiter plates, which may require longer assay times and increased reagent use. Amplification of nucleotides, such as, for example, polymerase chain reaction (PCR) is commonly used, for example, to increase the copy number of nucleic acids to determine the nucleotide sequence of deoxyribonucleic acid (DNA) and ribonucleic acid (RNA) molecules, to alter and mutate particular bases, to determine whether a particular sequence is found in a cell or organism, to introduce restriction enzyme sites, and to quantitatively measure DNA and RNA molecules.

Microarrays are another format for analyzing nucleic acids and proteins. For example, a DNA array is a collection of spots having a DNA fragment at each spot. Arrays allow for a complementary strand of DNA or RNA possibly found in a sample to bind to the spotted DNA to detect binding. Microarrays may also be used for gene expression profiling in which isolated RNA is converted to a labeled cDNA that is hybridized to an array and detected. Arrays may also be used with proteins such as, for example, antibodies to detect antibody-antigen interactions.

Screening large numbers of samples presents a number of problems such as the high cost of equipment, high reagent requirements for performing the assays, and high volumes of solutions. Microfluidics technology represents an emerging area that permits the control and manipulation of fluids at a very small scale as well as the design of systems using small volumes of fluid. Thus, microfluidic technology addresses some of the drawbacks associated with the high cost of equipment, high reagent requirements for performing dilution-based and diffusion-based assays, and the high volumes of solutions needed.

The supply of samples and reagents to microfluidic devices commonly use pressure-driven and electrokinetic-driven pumping methods. These methods, however, require external power sources and other equipment, which can lead to added expense and limit point-of-care applications where the added equipment is unavailable or is of limited access. Power-free microfluidic pumping methods such as, for example, droplet-based passive pumping, evaporation, capillary flow, and gravity-driven flow, do not require external power sources, but may be limited by other requirements such as, for example, device priming, specific temperature and humidity, and surface treatments. Additionally, degas-driven flow is a phenomenon used to manipulate fluids in poly(dimethylsiloxane)-based microfluidic devices that does not require external power.

A microfluidic platform that uses low fluid volume consumption, better process control, and requires no additional external equipment for its operation may reduce costs, reduce user error, provide faster analysis, and provide a universal assay for use in a range of different environmental contexts. Accordingly, there exists a continued need to develop alternative microfluidic devices and methods of using microfluidic devices.

SUMMARY OF THE DISCLOSURE

The present disclosure relates generally to devices and methods for using microfluidic devices. More particularly, the present disclosure relates to self-loading microfluidic devices. The present disclosure also relates to methods for determining therapeutically effective amounts of agents, determining minimum inhibitory concentrations, determining toxicity levels, and performing chemical and biological assays using self-loading microfluidic devices.

In one aspect, the present disclosure is directed to a self-loading microfluidic device. The self-loading microfluidic device includes a porous organic polymer and a reaction well, an inlet port, a vacuum well, a main channel and a side channel. In one aspect the self-loading microfluidic device includes a single layer of a suitable porous organic polymer, wherein the single layer includes a reaction well, an inlet port, a vacuum well, a main channel and a side channel. In another aspect, the self-loading microfluidic device includes a porous organic polymer and a plurality of layers. The plurality of layers includes a chamber layer and a channel layer. The plurality of layers includes a reaction well, an inlet port, a vacuum well, a main channel, a side channel, and combinations thereof.

In another aspect, the present disclosure is directed to a self-loading microfluidic device including a porous organic polymer and a reaction well, a main channel, a side channel, an inlet port, and a vacuum well, wherein the self-loading microfluidic device has a flow rate of from about 0.25 nL/second to about 5 nL/second and a post-vacuum idle time of from less than about 30 seconds to about 10 minutes.

In another aspect, the present disclosure is directed to a method of performing an assay using a self-loading microfluidic device. The method includes adding an agent in liquid form to a reaction well of a chamber layer in a self-loading microfluidic device, wherein the self-loading microfluidic device further comprises a channel layer and a cover and wherein the channel layer comprises an inlet port, a vacuum well, a main channel, and a side channel; drying the liquid to form a dried agent; assembling the self-loading microfluidic by contacting the chamber layer, the channel layer, and the cover, wherein the side channel terminates at the reaction well; degassing the self-loading microfluidic device in a low-pressure environment; removing the degassed self-loading microfluidic device from the low-pressure environment; adding a sample solution to the inlet port; flowing the sample solution from the inlet port to fill the reaction well by degas-driven flow; incubating the self-loading microfluidic device; and analyzing the reaction well.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 29A-F is a translucent schematic illustration of the results showing bacterial identification using self-loading microfluidic devices as described in Example 7.

Figure 1:
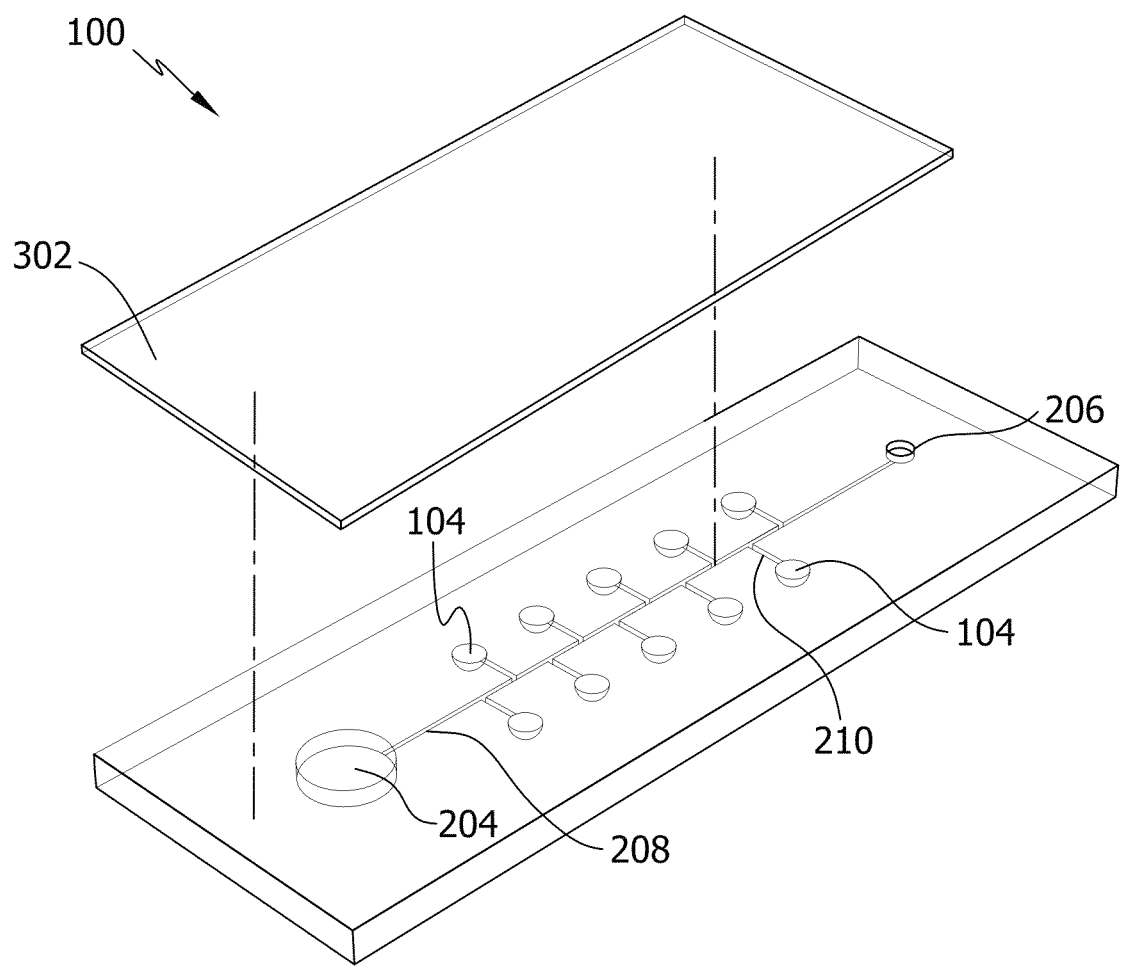
FIG. 1 is a translucent schematic illustration of a self-loading microfluidic device 100 having a single layer of a porous organic polymer that has a reaction well 104, an inlet port 206, a vacuum well 204, a main channel 208, a side channel 210 and a cover 302.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

In accordance with the present disclosure, self-loading microfluidic devices and methods for performing chemical and biological assays have been discovered. The devices further allow for multiple assays on one platform such as, for example, determining the effective amount of a therapeutic agent, nucleic acid amplification, nucleic acid detection, enzyme-substrate assays, detection assays, binding interaction assays, water quality testing, detection of organisms, and identification of organisms.

Self-Loading Microfluidic Devices

In one aspect, the present disclosure is directed to a self-loading microfluidic device. The self-loading microfluidic devices include a porous organic polymer and a reaction well, an inlet port, a vacuum well, a main channel and a side channel.

Any suitable porous organic polymer may be used to prepare the self-loading microfluidic device. Suitable porous organic polymers may be, for example, a silicon-based organic polymer. A particularly suitable silicon-based organic polymer is polydimethylsiloxane (PDMS). Other suitable organic polymers may be, for example, polyurethane, polyvinylchloride (PVC), polystyrene, polysulfone, polycarbonate, and polyolefins. Additionally, the self-loading microfluidic device may be prepared using a suitable thermoplastic material having sufficiently rapid air permeability and significant free volume. Thermoplastic self-loading microfluidic devices may, for example, be manufactured by polymer injection molding.

As shown in FIG. 1, the self-loading microfluidic devices 100 may be a single layer of a porous organic polymer having a reaction well 104, an inlet port 206, a vacuum well 204, a main channel 208, and a side channel 210. A cover 302 is placed over the single layer to seal the reaction well 104, the vacuum well 204, the main channel 208, and the side channel 210.

The self-loading microfluidic devices may include any number of reaction wells 104. The reaction well 104 may be any shape such as, for example, cylindrical, circular, spherical, square, rectangular, and triangular. The reaction well 104 may be of any desired diameter, any desired depth, and hold any desired volume. Suitable reaction well dimensions may be, for example, from about 10 μm to about 5 mm in diameter, from about 10 μm to about 1 mm in depth, and hold a volume of from about 1 pL to about 25 μL. The individual volume of the reaction well 104 is designed to be smaller than the individual volume of the vacuum well 204 such that a sample solution entering the main channel 208 through the inlet port 206 fills the reaction well 104 before the vacuum well 204.

The self-loading microfluidic devices include an inlet port 206. The inlet port 206 may be any shape such as, for example, cylindrical, circular, spherical, square, rectangular, and triangular. The inlet port may be of any desired diameter, any desired depth, and hold any desired volume. Suitable inlet port dimensions may be, for example, from about 100 μm to about 5 mm in diameter, from about 100 μm to about 1 cm in depth, and hold a volume of from about 1 nL to about 1 μL or more. The inlet port 206 and vacuum well 204 are connected by the main channel 208.

The self-loading microfluidic devices include a vacuum well 204. The vacuum well 204 may be any shape such as, for example, cylindrical, circular, spherical, square, rectangular, and triangular. The vacuum well may be of any desired diameter, any desired depth, and hold any desired volume. The individual volume of the vacuum well 204 is designed to be larger than the individual volume of the reaction well 104 and the inlet port 206 to drive the flow of the sample solution in the direction of the vacuum well 204 such that the sample solution enters the main channel 208 from the inlet port 206 to fill the reaction well 104. Suitable vacuum well 204 dimensions may be, for example, from about 20 μm to about 3 cm in diameter, 20 μm to about 1 cm in depth, and hold a volume of from about 10 nL to about 5 μL or more. The vacuum well 204 and inlet port 206 are connected by the main channel 208.

The self-loading microfluidic devices include a main channel 208. The main channel 208 connects the inlet port 206, the side channel 210, the reaction well 104, and the vacuum well 204. Suitable main channel 208 dimensions may be, for example, from about 5 µm to about 500 µm in height and from about 5 µm to about 1 mm wide.

The self-loading microfluidic devices include a side channel 210. The side channel 210 connects the main channel 208 and the reaction well 104. The side channel 210 dimensions may be, for example, from about 5 µm to about 500 µm in height and from about 5 µm to about 1 mm wide. The side channel is designed to be larger in diameter (height and width) than that of the main channel. Without being bound by theory, it is believed that a larger diameter side channel results in flow of the sample solution in the direction of the reaction well through the side channel. The side channel length should be sufficiently long to prevent diffusion of the agent in the first reaction well into other reaction wells. The side channels 210 are staggered such that when a sample solution flowing through the main channel 208 reaches a side channel 210, the sample solution is directed into the side channel 210. The sample solution flows in this manner until each of the reaction wells 104 is filled.

In another aspect, the self-loading microfluidic device includes a porous organic polymer and a plurality of layers. The plurality of layers includes a chamber layer 102 and a channel layer 202. The plurality of layers may include any combination of a reaction well 104, an inlet port 206, a vacuum well 204, a main channel 208 and a side channel 210.

At least one of the plurality of layers may be prepared from a porous organic polymer. For example, the chamber layer 102 may be prepared from a porous organic polymer layer. Alternatively, the channel layer 202 may be prepared from a porous organic polymer layer. In another aspect the chamber layer 102 and the channel layer 202 may be prepared from a porous organic polymer layer. In one aspect, the chamber layer 102 and the channel layer 202 may be prepared from the same porous organic polymer. In another aspect, the chamber layer 102 and the channel layer 202 may be prepared from different porous organic polymers.

Figure 2:
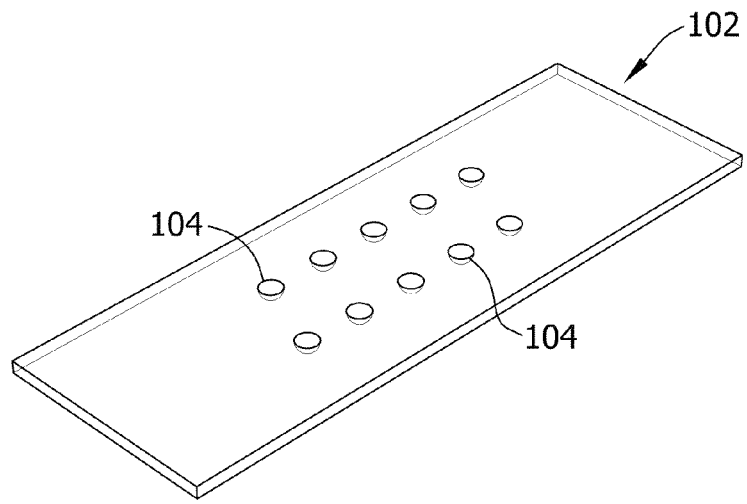
FIG. 2 is a translucent schematic illustration of a chamber layer 102 of an unassembled self-loading microfluidic device having a plurality of layers showing a chamber layer 102 with 10 reaction wells 104.
Figure 3:
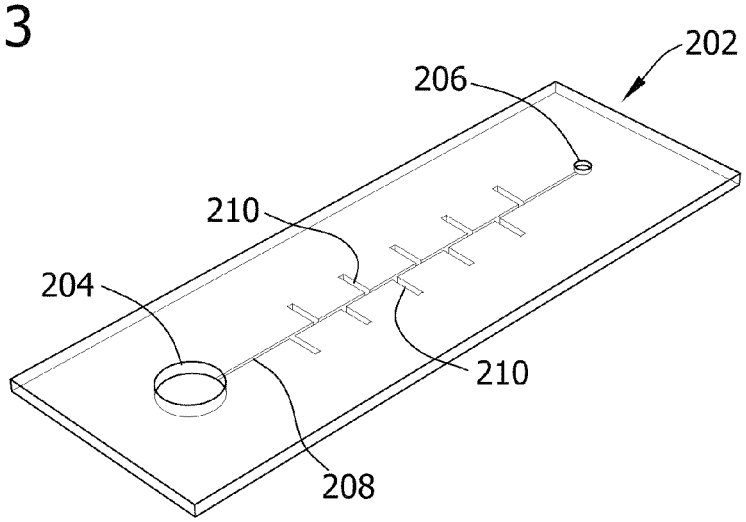
FIG. 3 is a translucent schematic illustration of a channel layer 202 of an unassembled self-loading microfluidic device having a plurality of layers showing a vacuum well 204, an inlet port 206, a main channel 208, and ten side channels 210.
Figure 4:
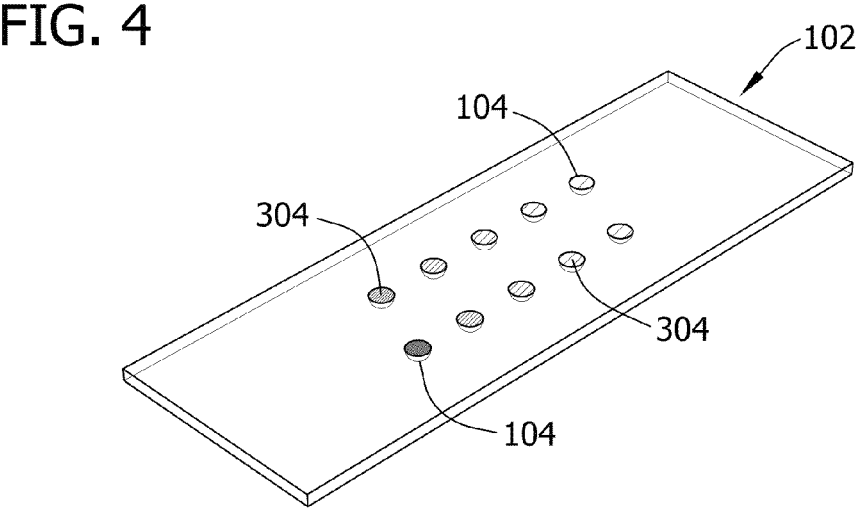
FIG. 4 is a translucent schematic illustration of a chamber layer 102 of an unassembled self-loading microfluidic device 100 having a plurality of layers showing a chamber layer 102 containing an agent in each reaction well 104.

As shown in FIGS. 2-4, the self-loading microfluidic device may include a plurality of layers having a chamber layer 102 and a channel layer 202. The chamber layer 102 may include, for example, a reaction well 104 wherein an agent 304 (FIG. 4) is added and an assay occurs. The reaction well 104 may be formed when the channel layer 202 is contacted with the chamber layer 102 during assembly of the self-loading microfluidic device, which seals the top of the reaction well 104. The chamber layer 102 may include any number of reaction wells 104.

The channel layer 202 may include, for example, a main channel 208 and any number of side channels 210. The channel layer 202 may also include an inlet port 206 for introducing a sample solution for a particular assay and a vacuum well 204 for collecting excess sample solution.

Figure 5:
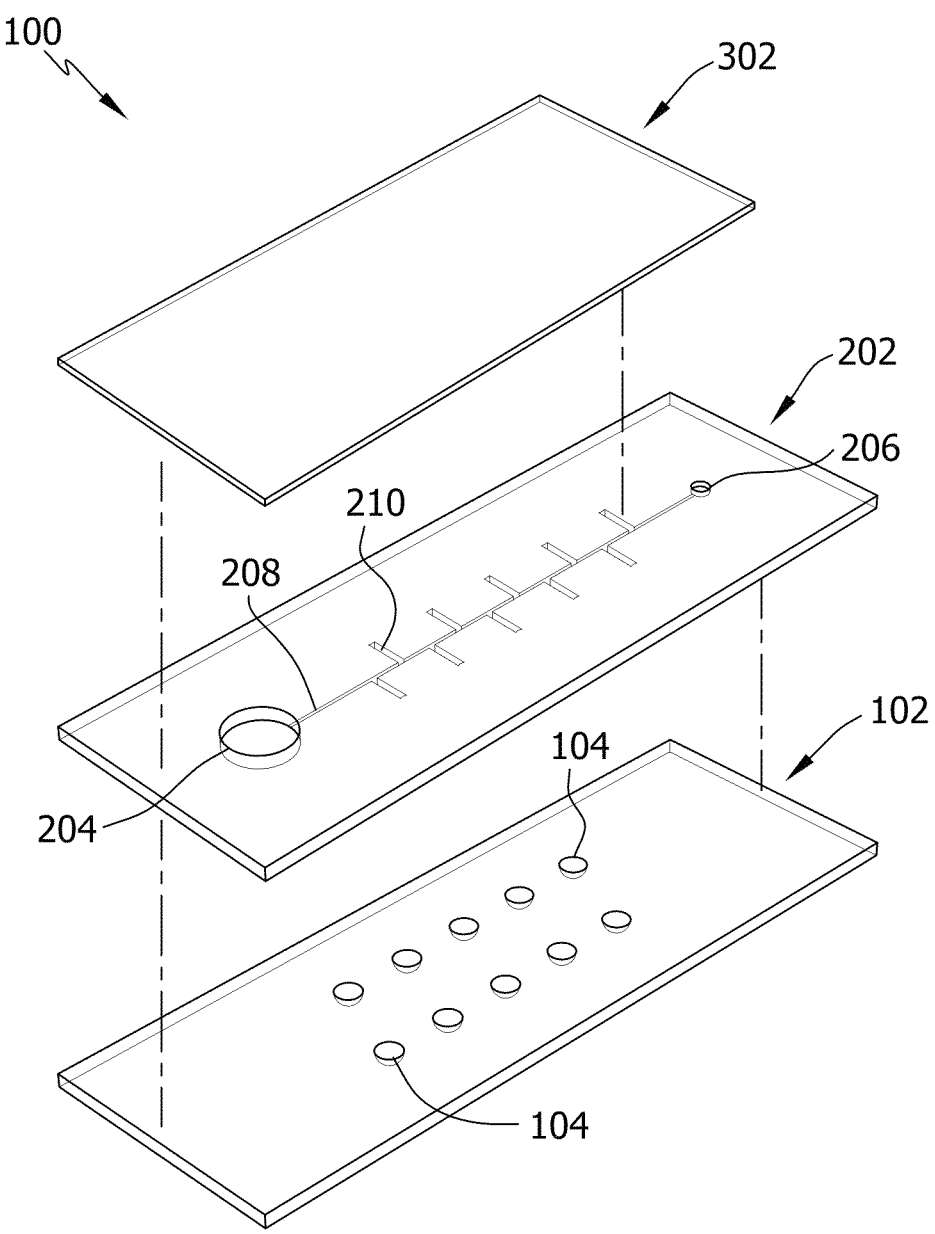
FIG. 5 is a translucent schematic illustration of a self-loading microfluidic device 100 having a plurality of layers showing the assembly of the device components including a chamber layer 102 having reaction wells 104, a channel layer 202 having a vacuum well 204, an inlet port 206, a main channel 208 and side channels 210, and a cover 302.
Figure 9:
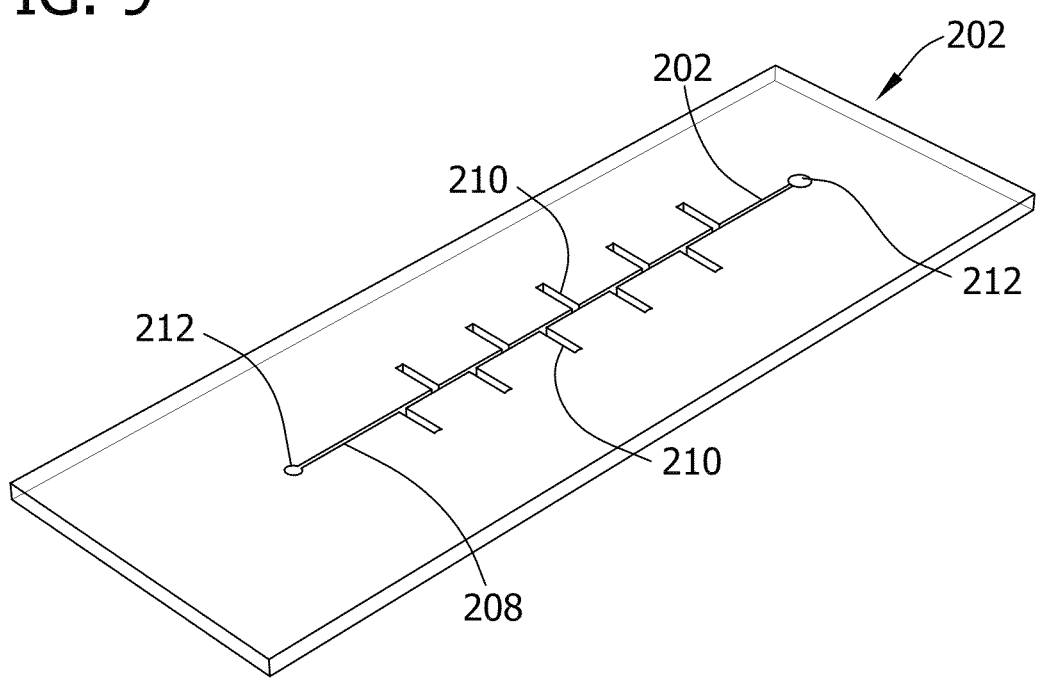
FIG. 9 is a schematic illustration of a channel layer 202 that has been peeled off a channel layer master template showing the main channel 208, side channels 210 and end spots 212.

As shown in FIG. 5, when the chamber layer 102, the channel layer 202 and the cover 302 of self-loading microfluidic device 100 are contacted to assemble the self-loading microfluidic device 100, the inlet port 206, the vacuum well 204, and the reaction wells 104 are connected by the main channel 208 and the side channel 210 (see, FIG. 9). When assembled in this manner, the sample solution can flow from the inlet port 206 into the main channel 208 and side channel 210 into the reaction well 104 because the side channel 210 ends (or terminates) in the reaction well 104.

The self-loading microfluidic device 100 may further include a cover 302 (as shown in FIGS. 1 and 5). Suitable covers 302 may be, for example, a glass slip, a plastic slip, a solid polymer layer, and adhesive tape. The inlet port 206 remains uncovered to facilitate the degas-driven flow of the sample solution as described herein.

The self-loading microfluidic device may optionally include packaging. In one aspect, the packaging may be vacuum-sealed packaging. Use of vacuum-sealed packaging may allow for a self-loading microfluidic device to be supplied in a ready-to-use form wherein an agent is added to the reaction well. After adding the agent to the reaction well as described herein, the self-loading microfluidic device is assembled and packaged into a vacuum-sealed packaging.

In one aspect, the self-loading microfluidic device may be supplied in an assembled form wherein an agent is added to a reaction well and dried, after which, the self-loading microfluidic devices is assembled, degassed and packaged in a vacuum-sealed packaging. Such pre-assembled forms of the self-loading microfluidic device may be made-to-order by a manufacturer to include any agent of interest, at any concentration of interest, and/or for any desired assay.

In another aspect, the self-loading microfluidic device may be supplied in an unassembled form. As used herein, an "unassembled" self-loading microfluidic device is one that is supplied in its component parts. For example, a single layer self-loading microfluidic device may be supplied as the porous organic polymer layer with or without a cover. A self-loading microfluidic device including a plurality of layers may be supplied as a chamber layer 102 and a channel layer 202 and, optionally, a cover 302. An unassembled self-loading microfluidic device may be supplied with some of its components bonded together as described herein. For example, the unassembled self-loading microfluidic device may be supplied with the cover 302 in contact with the channel layer 202. Alternatively, the unassembled self-loading microfluidic device may be supplied with the channel layer 202 in contact with the chamber layer 102. An unassembled self-loading microfluidic device may be supplied with or without including a dried agent in a reaction well 104. If the unassembled self-loading microfluidic device is supplied without a dried agent in a reaction well, the user may add an agent, dry the agent, assemble the self-loading microfluidic device, degas the device, and use the device as described herein.

Preparation of Self-Loading Microfluidic Devices

Figure 6:
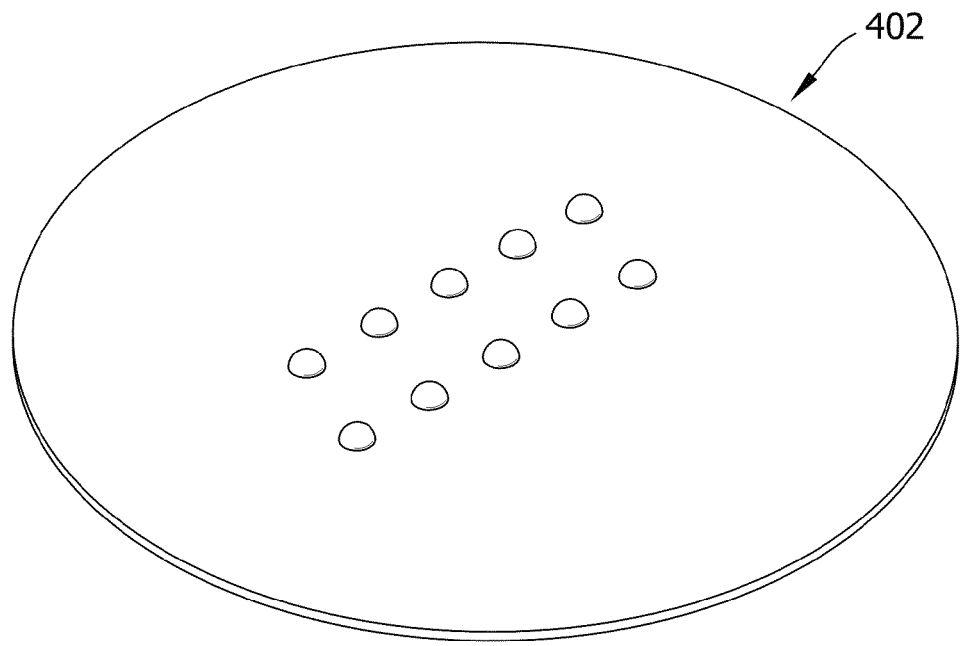
FIG. 6 is a schematic illustration of a reaction well layer master template for soft lithography.
Figure 7:
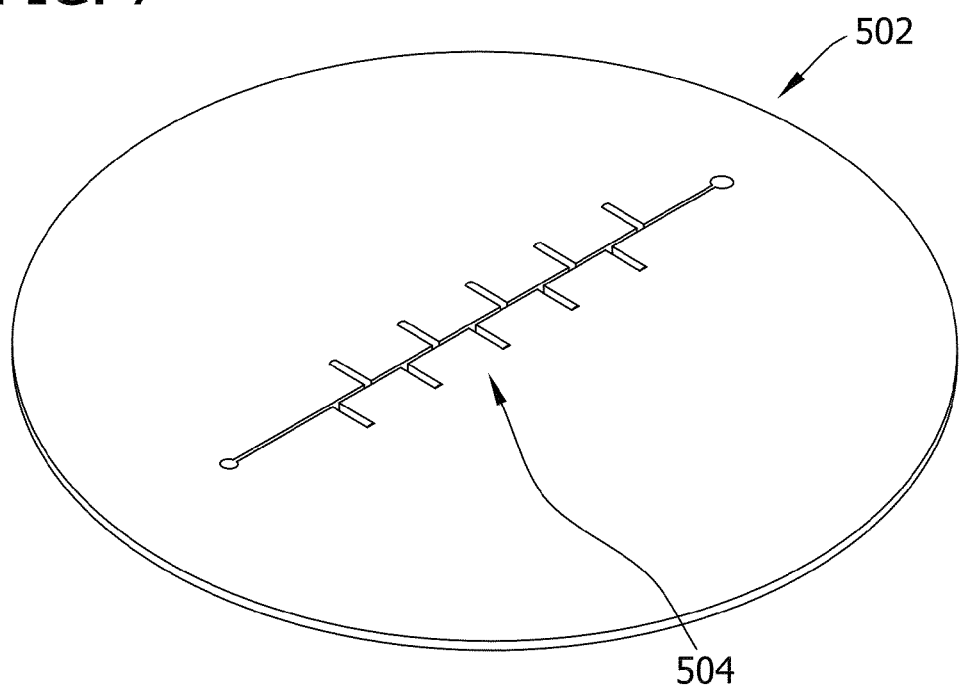
FIG. 7 is a schematic illustration of a channel layer master template for soft lithography.

In one aspect, the self-loading microfluidic devices may be fabricated using soft lithography. As shown in FIGS. 6 and 7, soft lithography uses master templates 402 and 502 that serve as stamps or molds for the respective layers that form the microfluidic device. The master templates may be fabricated using any suitable material. Suitable materials may be, for example, SU-8 photoresist (Microchem) on silicon wafers. Other materials include metals, Shipley photoresist, poly(m-ethylmethacrylate), polycarbonate, epoxy, and polyurethane.

As shown in FIGS. 6-9, to prepare a self-loading microfluidic device including a plurality of layers that has a chamber layer and a channel layer, a chamber layer master template 402 and a channel layer master template 502 are prepared. The chamber layer master template 402 is prepared by depositing photoresist in the shape of a reaction well 104 onto a silicon wafer to form a negative. The dimensions of the photoresist for forming the reaction wells may be of any desired height and diameter or width, and may be readily determined by those skilled in the art. The reaction well may also be any desired shape. The channel layer master template 502 is prepared by depositing photoresist in the shape of channels 504 onto a silicon wafer to form a negative. The dimensions of the photoresist for forming the channels 504 of the channel layer master template 502 may be of any desired height and width, and may be readily determined by those skilled in the art.

Figure 8:
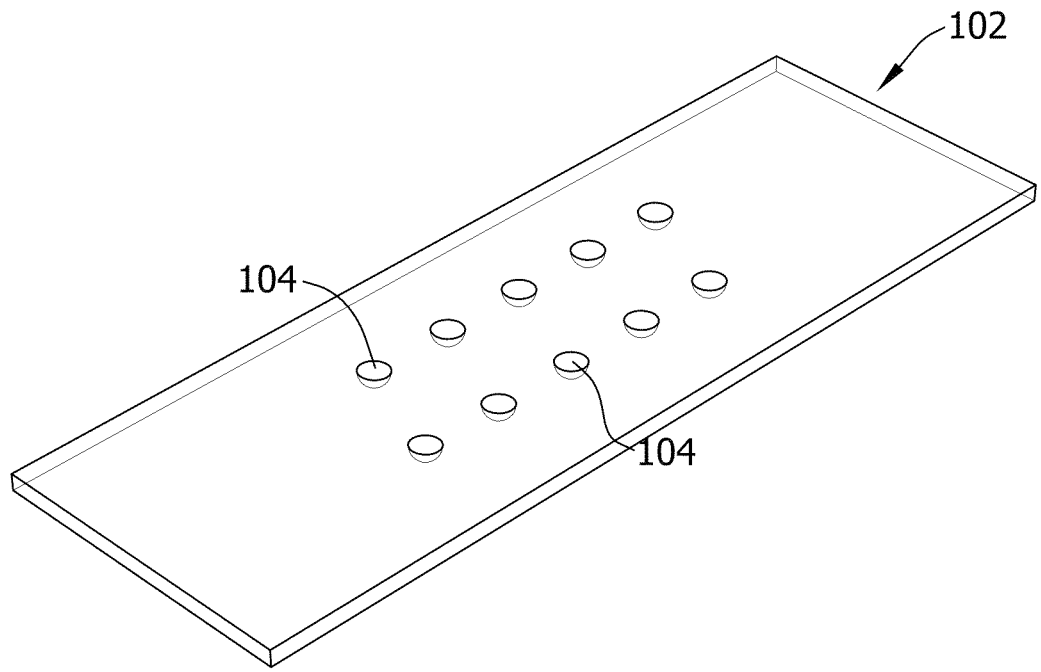
FIG. 8 is a schematic illustration of a chamber layer 102 that has been peeled off a chamber layer master template showing reaction wells 104.

After preparing the master templates 402 and 502, a suitable porous organic polymer is cast onto the master templates. The cured porous organic polymer is then peeled off of the master template. As shown in FIG. 8, the layer peeled away from the chamber layer master template 402 (shown in FIG. 6) forms the chamber layer 102 having reaction wells 104. As shown in FIG. 9, the layer peeled away from the channel layer master template 402 (shown in FIG. 7) forms the channel layer 202 having a main channel 208 and side channels 210. To form the inlet port 206 and vacuum well 204 of the channel layer 202, holes are punched at the end spots 212 of the main channel 208 using methods known to those skilled in the art. The chamber layer 102 and channel layer 202 may be trimmed to any desired size and shape.

Device Assembly

To assemble the self-loading microfluidic device, an agent is added into a reaction well. As used herein, the term "agent" refers to the collection of compounds used in a chemical assay or a biological assay. Suitable agents may be, for example, therapeutic agents, reagents, proteins, nucleic acids, peptide-nucleic acid conjugates, peptoids, cells, cell extracts, naturally produced metabolites, low-molecular weight organic molecules, polymers, antibiotics, antibodies, viruses, sugars, metabolites, and combinations thereof. Suitable therapeutic agents may be, for example, any type of drug, drug candidates, medicines, pharmaceuticals, biologics, proteins, small molecule drugs, antibodies, etc., used for studying, treating, controlling, or preventing diseases or medical conditions. Particularly suitable therapeutic agents may be, for example, chemotherapeutics, small molecule drugs, antibiotics, toxins, anti-viral compounds, inhibitors, proteins, nucleic acids, genes, gene fragments, hormones, and growth factors. Suitable reagents may be, for example, enzymes, enzyme inhibitors, pH indicators, substrates, catalysts, chromophores, fluorochromes, buffers, nucleic acids, ions, and combinations thereof. Suitable proteins may be, for example, amino acids, peptides, peptide-nucleic acid conjugates, peptoids, polypeptides, protein fragments, full-length proteins, recombinant proteins, synthesized proteins, and combinations thereof. Particularly suitable proteins may be, for example, monoclonal antibodies, polyclonal antibodies, antibody fragments such as, for example, antigen binding domains, biomarker proteins, biomarker peptides, and protein binding partners. Suitable nucleic acids may be, for example, DNA, RNA, plasmids, vectors, oligonucleotides, primers, peptide-nucleic acid conjugates, and nucleotides (e.g., adenine, guanine, cytosine, thymine, and uracil).

The agent is added into the reaction well in liquid form. The liquid is then removed from the reaction well using any suitable method. Suitable methods may be, for example, by evaporating the liquid by placing the chamber layer in a laminar flow hood or by lyophilization. The agent should be sufficiently dry such that liquid is not expelled from the reaction wells during degassing.

Figure 10:
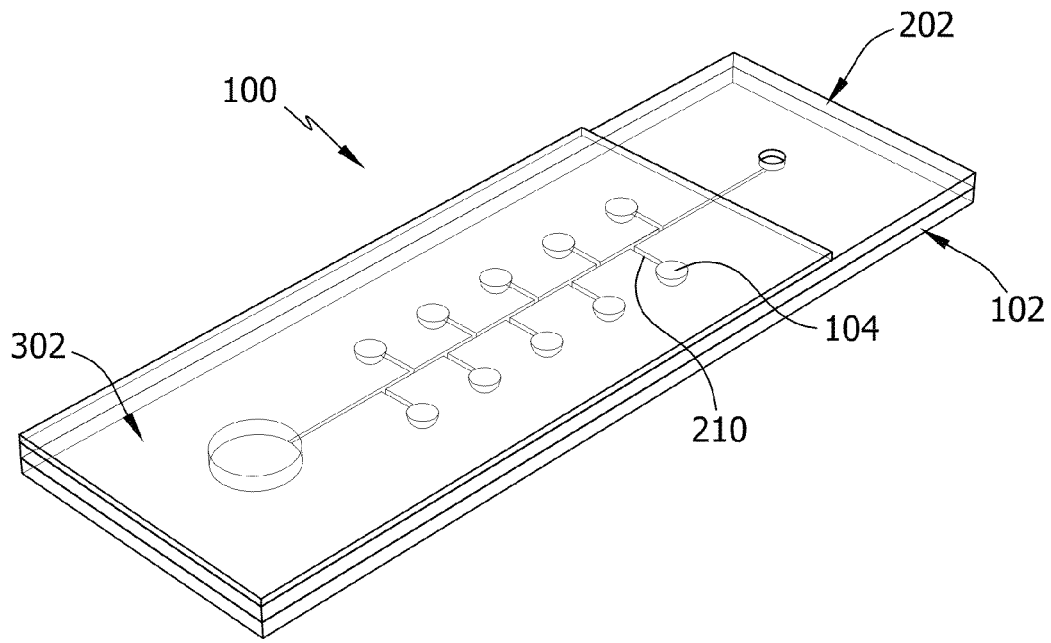
FIG. 10 is a translucent schematic illustration of an assembled self-loading microfluidic device 100 having a plurality of layers showing a chamber layer 102 and a channel layer 202 with side channels 210 terminating at reaction wells 104 and a cover 302.

After the agent is dried, the components of the self-loading microfluidic device are assembled. As used herein, the terms "assembled", "assemble", and "assembly" are used according to their ordinary meaning to refer to contacting the components of the self-loading microfluidic device together as described herein. As shown in FIG. 5 for a self-loading microfluidic device including a plurality of layers, for example, the channel layer 202 is contacted with the chamber layer 102 such that a side channel 210 terminates or ends in a reaction well 104. The reaction well 104 is connected to the inlet port 206 and vacuum well 204 by the side channel 210 and the main channel 208. A cover 302 is contacted with the channel layer 202 such that the cover 302 is positioned over the vacuum well 204. As shown in FIG. 10, only the inlet port 206 remains open to the outside environment to facilitate sample loading.

The channel layer 202 and chamber layer 102 may be reversibly or irreversibly bonded together. The channel layer 202 and chamber layer 102 may be reversibly bonded by merely contacting the channel layer 202 to the chamber layer 102. Alternatively, a bonding agent that allows for reversibly adhering the layers may be used. The channel layer 202 and chamber layer 102 may be irreversibly bonded by applying a bonding agent to all or part of the channel layer 202 and/or the chamber layer 102 prior to contacting the channel layer 202 to the chamber layer 102. Suitable bonding agents for irreversibly bonding the layers may be, for example, PDMS, epoxy, and treating the PDMS layers with an oxygen plasma to render them hydrophilic and reactive.

The self-loading microfluidic device is then degassed to remove air and water vapor from the porous organic polymer layer by placing the device in a vacuum well. Air and water vapor contained in the polymer of the device is removed by maintaining the self-loading microfluidic device at a low pressure (less than about 0.3 atm).

The self-loading microfluidic device may be used after degassing or may be housed in a vacuum-sealed container until use. After removing the self-loading microfluidic device from the low-pressure environment following degassing or removal from its vacuum-sealed packaging, the self-loading microfluidic device will reabsorb gas until it reaches equilibrium with the atmosphere. Upon reaching equilibrium with the atmosphere, the device will no longer exhibit degas-driven flow. Therefore, to fill the device using degas-driven flow, the sample solution is added to the inlet port at any time point before the degassed device reaches equilibrium with the atmosphere.

The post-vacuum idle time affects the amount of air present in the porous organic polymer, and thus, the pressure difference that drives the degas-driven flow rate. As used herein, the "post-vacuum idle time" refers to the time the self-loading microfluidic device is removed from the low-pressure environment to the time a sample solution is added to the inlet port. A short post-vacuum idle time may result in faster flow rate, whereas long post-vacuum idle time may result in slower flow rate. It is within the skill of those in the art to determine the post-vacuum idle time for achieving the desired flow rate. Particularly suitable post-vacuum times may be from less than about 30 seconds to about 10 minutes. If an even slower flow rate is desired, the post-vacuum idle time may be for longer than 10 minutes to a time before the device reaches equilibrium with the atmosphere.

Method of Filling a Self-Loading Microfluidic Device

Figure 11:
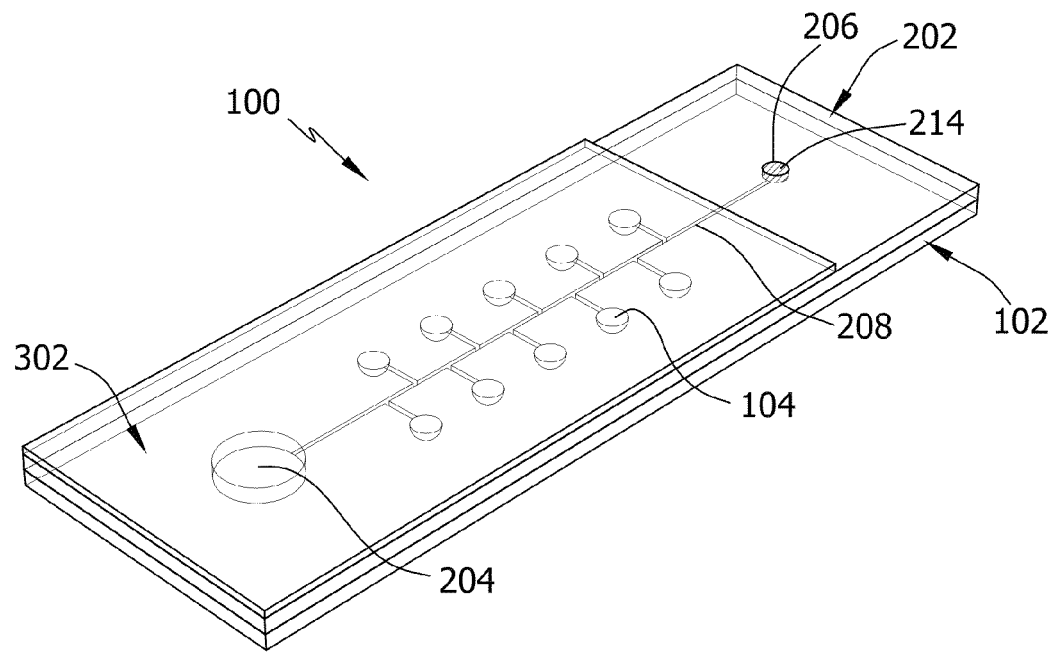
FIG. 11 is a translucent schematic illustration of an assembled self-loading microfluidic device having a plurality of layers and containing a sample solution in the inlet port 214.
Figure 12:
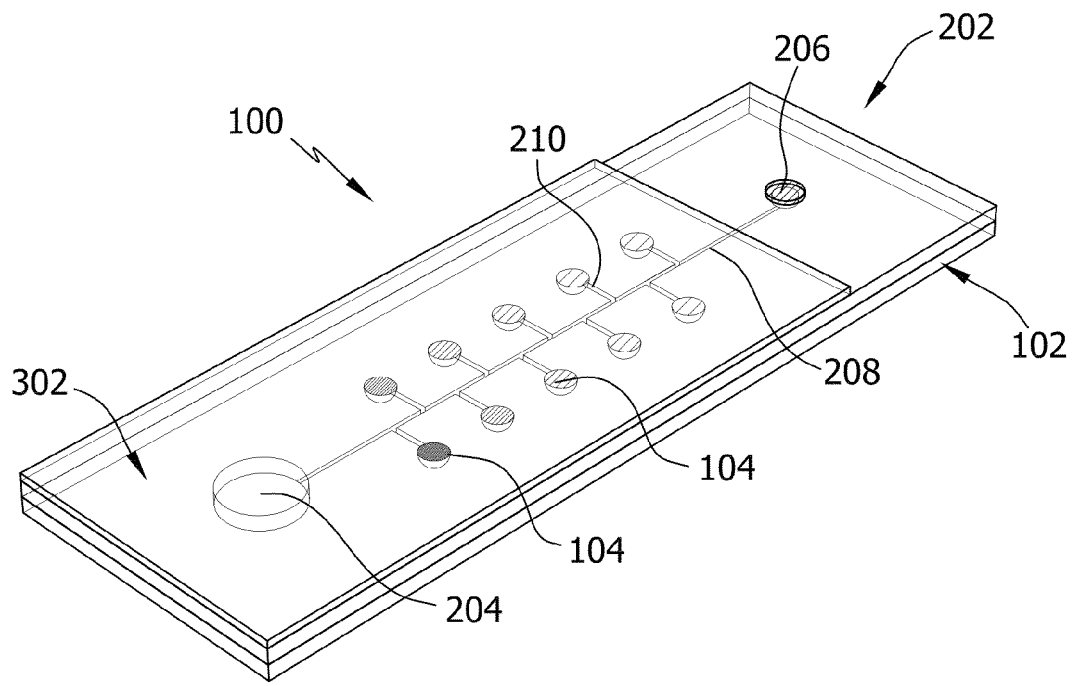
FIG. 12 is a translucent schematic illustration of an assembled self-loading microfluidic device having a plurality of layers and an increasing concentration (indicated by increasing density of hatching) of an agent in each reaction well 104 and a sample solution in the inlet port 206.
Figure 13:
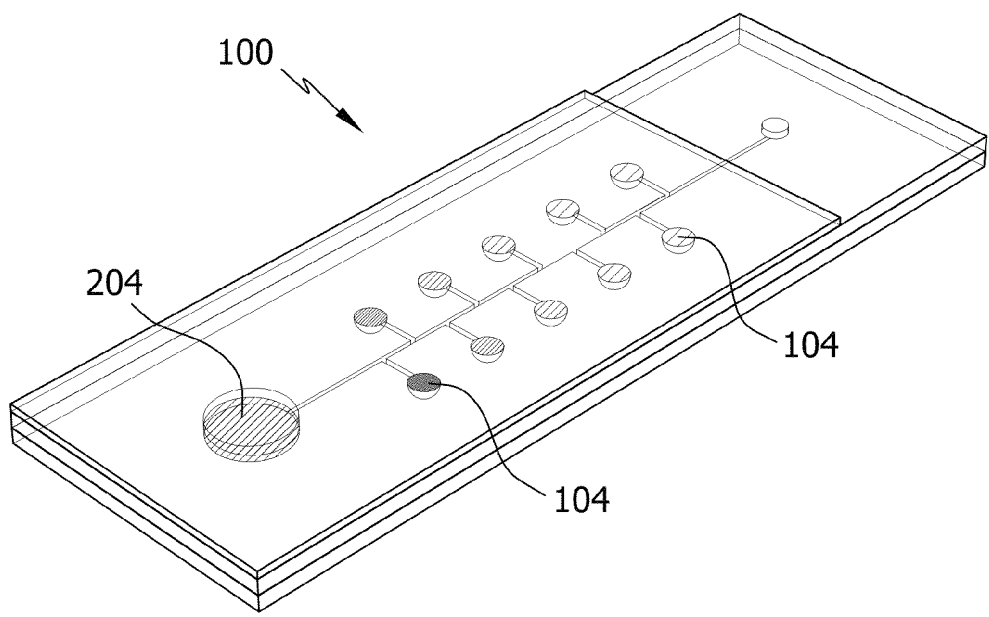
FIG. 13 is a translucent schematic illustration of an assembled self-loading microfluidic device 100 having a plurality of layers in which the sample solution from the inlet port has filled each reaction well 104 having an increasing concentration (indicated by increasing density of hatching) of an agent and excess sample solution collected in the vacuum well 204.
Figure 14:
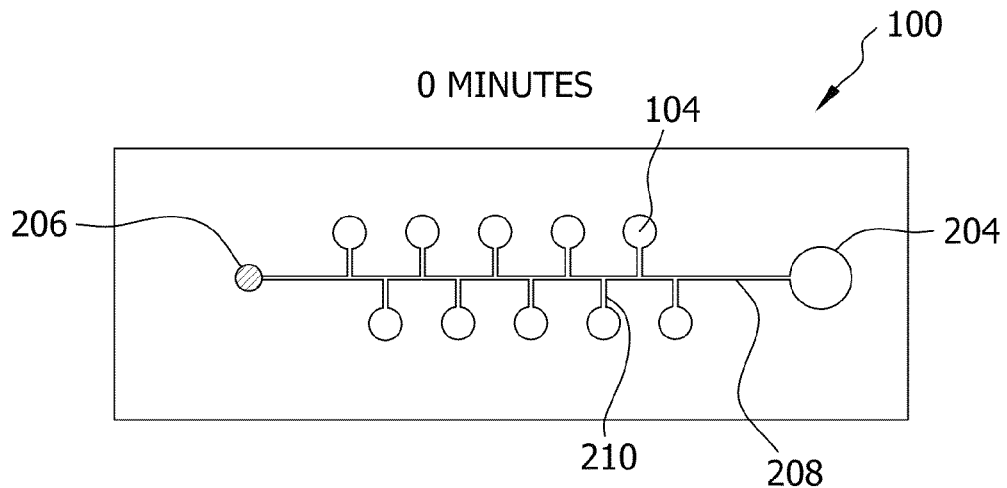
FIG. 14 is a translucent schematic illustration of the sample flow in a self-loading microfluidic device after a sample solution has been added to the inlet port 206 (time 0 minutes) and is drawn toward the vacuum well 204.
Figure 15:
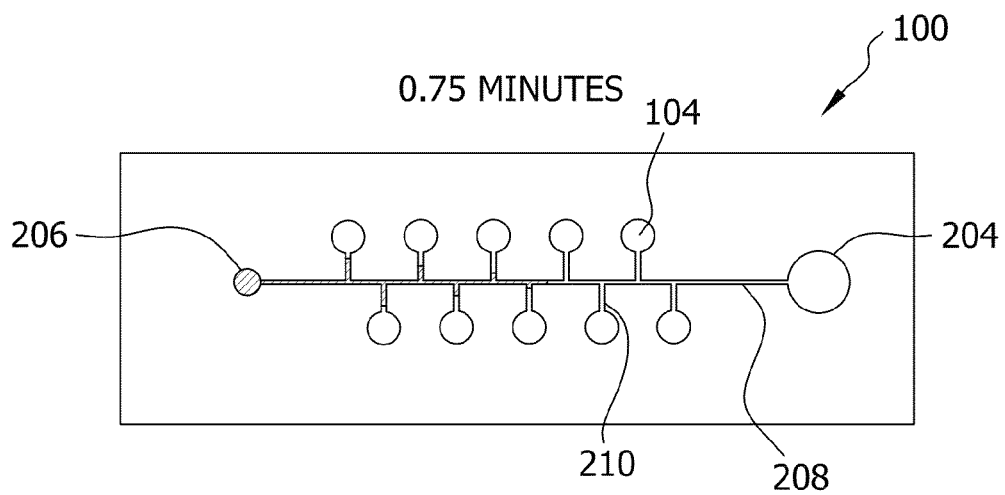
FIG. 15 is a translucent schematic illustration of the sample flow in a self-loading microfluidic device showing the flow of a sample solution at 0.75 minutes after the sample solution was added to the inlet port 206 and is drawn toward the vacuum well 204.
Figure 16:
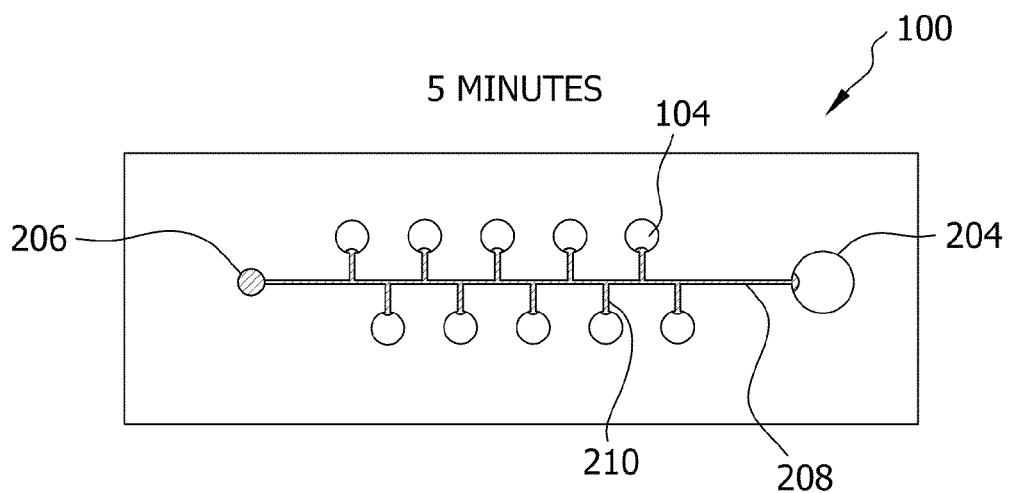
FIG. 16 is a translucent schematic illustration of the sample flow in a self-loading microfluidic device showing the flow of a sample solution at 5 minutes after the sample solution was added to the inlet port 206 and excess sample solution is beginning to enter the vacuum well 204.
Figure 17:
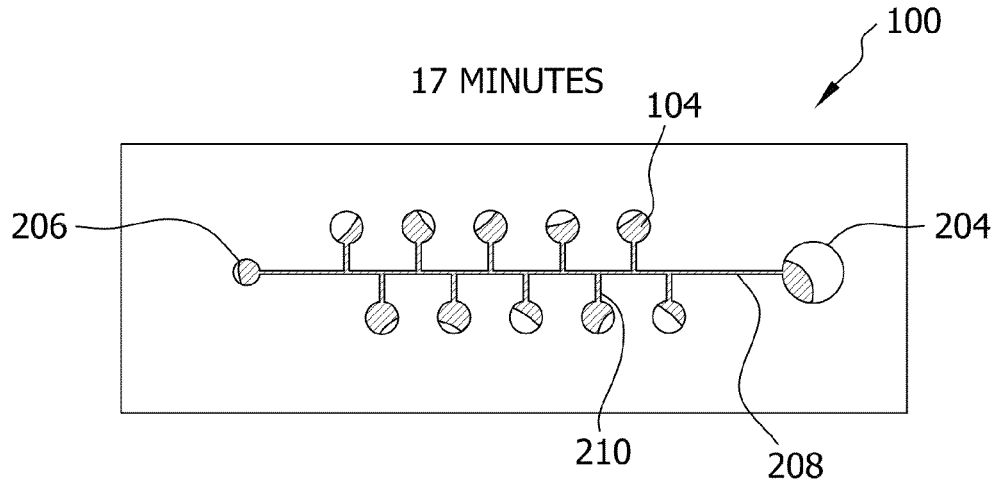
FIG. 17 is a translucent schematic illustration of the sample flow in a self-loading microfluidic device 100 showing the flow of a sample solution at 17 minutes after the sample solution was added to the inlet port 206.
Figure 18:
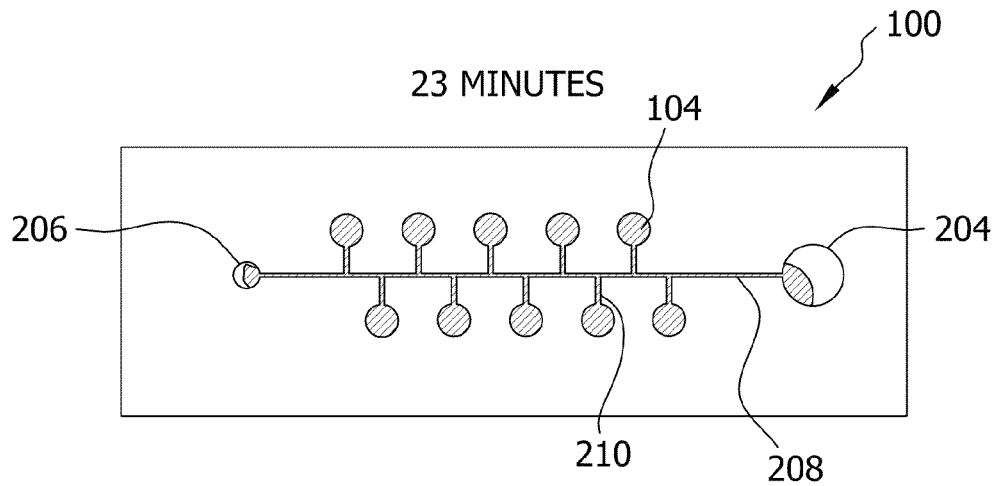
FIG. 18 is a translucent schematic illustration of the sample flow in a self-loading microfluidic device 100 showing the flow of a sample solution at 23 minutes after the sample solution was added to the inlet port 206.

The reaction well of the self-loading microfluidic device is filled using degas-driven flow. Degas-driven flow does not require external power, but rather takes advantage of the high porosity and air solubility of porous materials by removing air molecules from the porous materials before initiating the flow. Removing air from the porous material creates a pressure difference relative to atmospheric pressure. Upon return to atmospheric pressure, the pressure difference causes air inside the channels to diffuse into the porous material. Because the vacuum well 204 is sealed, for example with a cover 302, and the side channel 210 terminates at a reaction well 104, a dead-end channel system is formed in which side channels 210 end at reaction wells 104 and the main channel 208 ends at the vacuum well 204 (see, FIGS. 11 and 12). When the sample solution is added to the inlet port 206 to form a sample solution-filled inlet port 214 (FIG. 11), the sample solution seals the channels system (side channels 210 and main channel 208). Absorption of air into the degassed material from the reaction well 104, vacuum well 204, side channels 210 and main channel 208 draws the sample solution from the sample solution-filled inlet port 214 into the main channel 208. When the sample solution in the main channel 208 reaches the first side channel 210, the sample solution is drawn through the side channel 210 to fill the reaction well 104. The volume of the reaction well 104 is smaller than the volume of the vacuum well 204 such that the sample solution enters the reaction well 104 before the vacuum well 204. The length of the side channel 210 from the main channel 208 to the reaction well 104 may be designed to be sufficiently long to prevent diffusion of any agent contained in one reaction well 104 into another reaction well 104.

In one aspect, the cross-sectional area of the side channel 210 is greater than the cross-sectional area of the main channel 208. A particularly suitable cross-sectional area of a side channel 210 is about two times the cross-sectional area of the main channel 208. Because the cross-sectional area of the side channel 210 is greater than the cross-sectional area of the main channel 208, the flow rate of the side channel 210 is more rapid that the flow rate of the main channel 208, which contributes to the sample solution flow in the direction of the reaction well 104 through the side channel 210. This may also contribute to rapid filling of the reaction well 104 as the sample solution continues to flow through the main channel 208 in the direction of the vacuum well 204 and other reaction wells 104.

In another aspect, the cross-sectional area of the side channel and main channel may increase distal to the inlet port. In such an aspect, the cross-sectional area of the main channel at a point closest (proximal) to the inlet port will be smaller than the cross-sectional area at a point further (distal to) from the inlet port. Without being bound by theory, a larger cross-sectional area distal to the inlet port may result in a more rapid flow rate through the main channel. In another aspect, the cross-sectional area of a side channel may increase distal to the inlet port. Thus, the cross-sectional area may increase in each side channel in a multi-side channel device such that each side channel becomes greater. In this aspect, for example, the cross-sectional area of the side channel closest to the inlet port would be greater than the cross-sectional area of the side channel closest to the vacuum well. In still another aspect, the cross-sectional area of an individual side channel may increase from the main channel to the reaction well. In this aspect, for example, the cross-sectional area at the point closest to the main channel would be smaller than the cross-sectional area of the side channel at the point closest to the reaction well.

Figure 19:
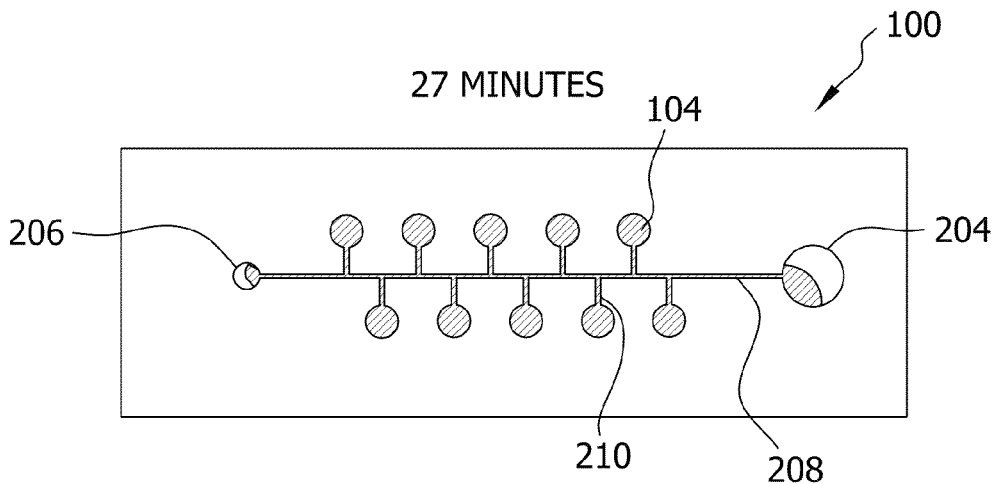
FIG. 19 is a translucent schematic illustration of the sample flow in a self-loading microfluidic device 100 showing the flow of a sample solution at 27 minutes after the sample solution was added to the inlet port 206.
Figure 20:
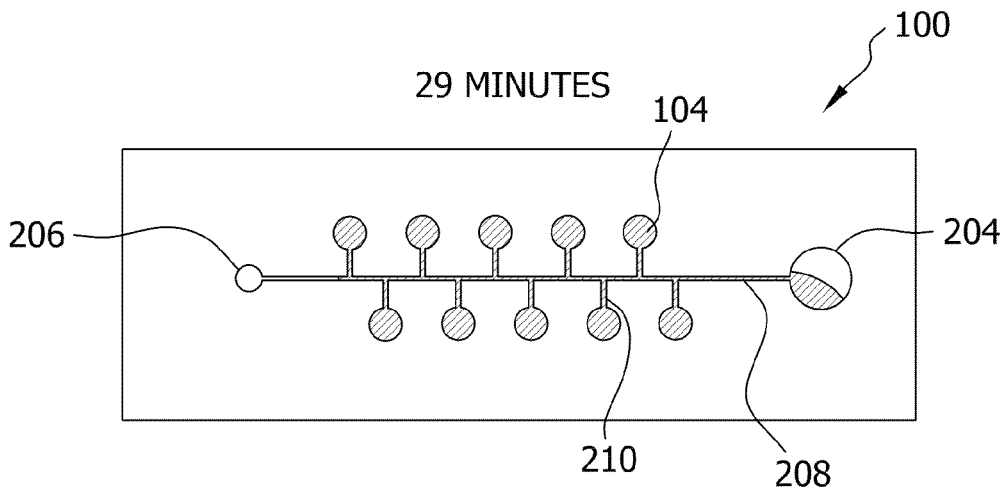
FIG. 20 is a translucent schematic illustration of the sample flow in a self-loading microfluidic device 100 showing the flow of a sample solution at 29 minutes after the sample solution was added to the inlet port 206.
Figure 21:
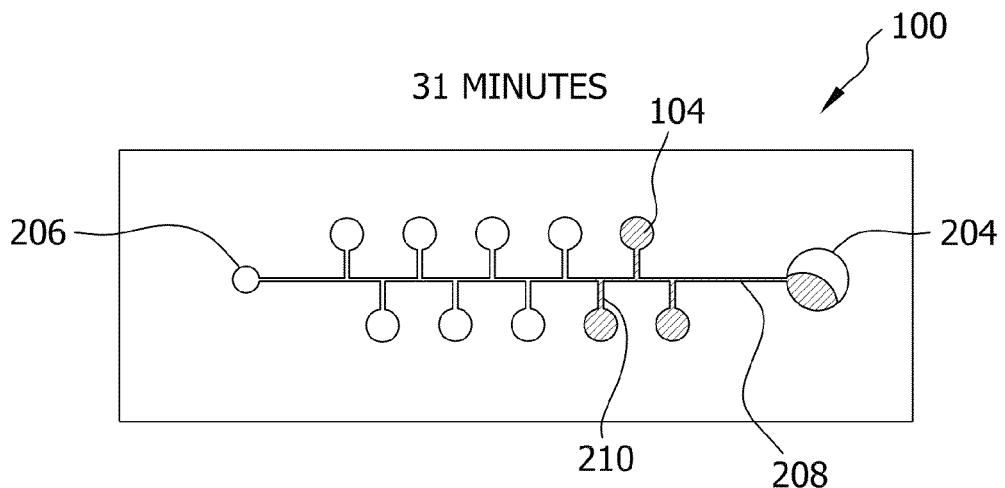
FIG. 21 is a translucent schematic illustration of the sample flow in a self-loading microfluidic device 100 showing the flow of a sample solution at 31 minutes after the sample solution was added to the inlet port 206.
Figure 22:
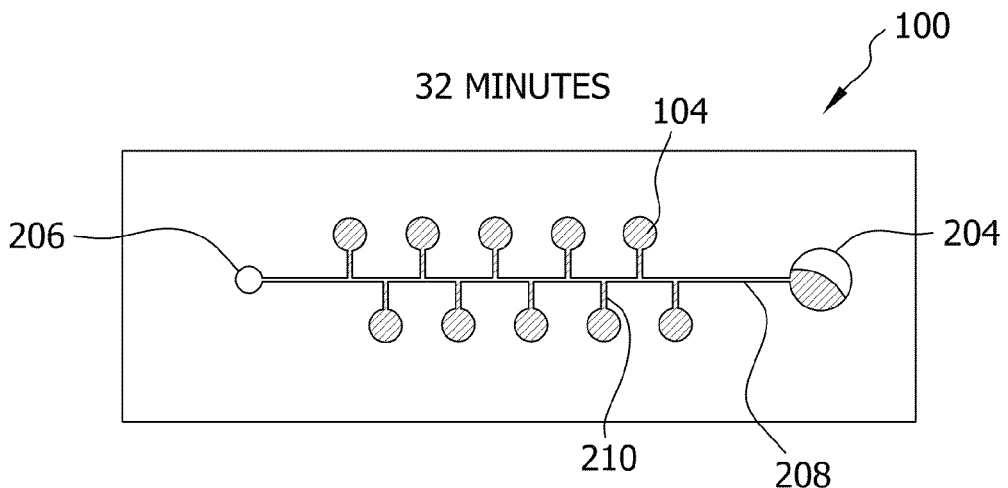
FIG. 22 is a translucent schematic illustration of the sample flow in a self-loading microfluidic device 100 showing the flow of a sample solution at 32 minutes after the sample solution was added to the inlet port 206.

As illustrated by FIGS. 12-22, when a sample solution is added to the inlet port 206, the pressure decrease relative to atmospheric pressure inside the channels, the reaction wells 104 and vacuum well 204 pulls the sample solution from the inlet port 206 into the main channel 208 of the self-loading microfluidic device. As the sample solution reaches a side channel, the sample solution flows through the side channel 210 and into the reaction well 104 located at the end of the side channel 210. As the reaction well 104 fills with the sample solution, the agent that has been dried is dissolved or resuspended by the sample solution such that an assay may occur. These flow dynamics occur until each reaction well 104 is filled. Degas-driven flow continues to pull the sample solution into the vacuum well 204 until the sample solution in the inlet port 206 is consumed (FIGS. 19-21). Excess sample solution also fills the vacuum well 204. Once the sample solution in the inlet port 206 is consumed an influx of air provides a physical barrier that isolates the sample solution and compartmentalizes the individual reaction wells 104. Alternatively, a solution that is immiscible in the sample solution may be used to create a physical barrier that isolates and compartmentalizes the individual reaction wells. Suitable solutions that may be used to create a barrier include, for example, oil (mineral oil, vegetable oil, silicone oil) and fluorinated alkanes. Compartmentalization of individual reaction wells 104 continues as the physical barrier isolates each filled reaction well 104 (FIG. 22). Excess sample flows into and collects in the vacuum well 204.

Various parameters may affect the dynamics of degas-driven flow (see for example, Beebe et al. Annu. Rev. Biomed. Eng. 4:261-286 (2002)), which is incorporated by reference). For example, device geometries, channel geometries, thickness of the porous material, exposure area, vacuum degassing time, and time at atmospheric pressure (post-vacuum idle time) prior to loading may affect degas-driven flow.

In one aspect, the present disclosure is directed to a self-loading microfluidic device comprising a porous organic polymer, a reaction well, an inlet port, a vacuum well, a main channel, and a side channel, wherein the self-loading microfluidic device has a flow rate of from about 0.25 nL/second to about 5 nL/second and a post-vacuum idle time of from less than about 30 seconds to about 10 minutes. In another aspect, the self-loading microfluidic device may have a flow rate of from about 0.5 nL/second to about 3 nL/second.

Methods of Screening Using Microfluidic Devices

In another aspect, the present disclosure is directed to a method of performing an assay using a self-loading microfluidic device. The method includes adding an agent in liquid form to a reaction well of a chamber layer in a self-loading microfluidic device, wherein the self-loading microfluidic device further comprises a channel layer and a cover and wherein the channel layer comprises an inlet port, a vacuum well, a main channel, and a side channel; drying the liquid to form a dried agent; assembling the self-loading microfluidic by contacting the chamber layer, the channel layer, and the cover, wherein the side channel terminates at the reaction well; degassing the self-loading microfluidic device in a low-pressure environment; removing the degassed self-loading microfluidic device from the low-pressure environment; adding a sample solution to the inlet port; flowing the sample solution from the inlet port to fill the reaction well by degas-driven flow; incubating the self-loading microfluidic device; and analyzing the reaction well.

The self-loading microfluidic devices of the present disclosure are particularly useful for methods of performing a variety of chemical assays and biological assays. The method involves the preparation of a self-loading microfluidic device as described herein. The methods generally include the introduction of an agent in liquid form into a reaction well of the self-loading microfluidic device. After the liquid is removed, the device is assembled and degassed. Upon removal from low atmospheric pressure conditions and following any post-vacuum idle time, a sample solution is introduced into the inlet port and the sample solution fills the reaction well. The sample solution resuspends or dissolves the agent and the assay begins. During and/or upon completion of the assay, the reaction may be monitored by detection of the assay result.

Analysis of the reaction may include the detection of a signal. The detectable signal may be, for example, a fluorescent signal, a luminescent signal, and a colorimetric signal. Monitoring of the signals may be performed using an optical detection system. For example, fluorescence based signals are typically monitored using, for example, laser activated fluorescence detection systems which employ a laser light source at an appropriate wavelength for activating the fluorescent indicator within the system. Fluorescence is then detected using an appropriate detector element, for example, a photomultiplier tube (PMT). Similarly, for assays using colorimetric signals, spectrophotometric detection systems may be employed that direct a light source at the sample and provide a measurement of absorbance or transmission of the sample.

A wide variety of chemical assays and biological assays may be conducted using the self-loading microfluidic device. For example, molecule identification, receptor-ligand interactions, enzyme-substrate interactions, cellular signaling pathways, and cellular responses may be conducted. Particularly suitable chemical assays and biological assays may be, for example, determining the minimum inhibitory concentration of an antibiotic, organism identification, immunoassays, amplification of a nucleic acid, detection of a nucleic acid, protein-protein interactions, DNA-protein interactions, DNA-RNA interactions, RNA-protein interactions, and RNA-RNA interactions.

Suitable biological assays may be, for example, determining a minimum inhibitory concentration of an antibiotic, determining a therapeutically effective amount of a drug, determining an effect of a drug on a cell, virus, or multicellular organism, determining an effect of a drug candidate on a cell, virus, or multicellular organism, identifying an organism, determining an antibody-antigen interaction, determining an identity of an analyte, amplification of a nucleic acid, detection of a nucleic acid, and determining the concentration of cells, viruses, multicellular organisms, nucleic acids, proteins, through digital or real time quantification.

In another aspect, analysis of the reaction may be determining an effect of an agent on a cell. The cell may be capable of producing a detectable signal. Determining an effect of an agent on a cell may include viability (growth) of the cell.

In another aspect, the assay may be the identification of any molecule of interest. Molecules that may be identified may be, for example, a biological molecule, a chemical molecule, and combinations thereof. Biological molecules may be, for example, cells, viruses, bacteria, fungi, spores, toxins, proteins, peptides, amino acids, antigens, nucleic acids, polynucleotides, oligonucleotides, ligands, drug, and other biological molecules of interest. Chemical molecules may be, for example, drugs, toxins, and other chemicals of interest.

In one particularly suitable aspect, the self-loading microfluidic device may be used to identify an organism. Particularly suitable organisms to be identified may be bacteria. For example, different agents such as sugar compounds that are known by those skilled in the art to support the growth of particular bacterial organisms may be dried in a reaction well of the self-loading microfluidic device of the present disclosure. A sample solution containing an unknown bacteria may be loaded in the inlet port and each reaction chamber that includes a different sugar may be monitored for identification of the bacteria contained in the unknown sample solution.

In another aspect, the microfluidic devices may be used for amplification assays. In amplification assays, agents for performing amplification are added to a reaction well. Any of the agents for the assay may be added to the reaction well such as, for example, buffers, nucleotides, oligonucleotides, vectors, and plasmids. As described herein, the agents are dried to remove the liquid by any suitable method for removing the liquid. For example, the liquid may be evaporated or lyophilized. Upon loading of the sample into the input port and subsequent flow through the channels into the reaction wells, the sample solution will resuspend and mix the reaction components. The microfluidic device is incubated for a period of time such that the reaction can proceed and until a point at which a signal is detected.

Particularly suitable amplification assays that use the device include isothermal amplification. Isothermal amplification is generally conducted without the need of a thermocycling apparatus. Suitable types of isothermal amplification may be, for example, transcription mediated amplification, nucleic acid sequence-based amplification, signal mediated amplification, strand displacement amplification, rolling circle amplification, loop-mediated isothermal amplification, isothermal multiple displacement amplification, helicase-dependent amplification, single primer isothermal amplification, and circular helicase-dependent amplification.

The disclosure will be more fully understood upon consideration of the following non-limiting Examples.

EXAMPLES

Example 1

Fabrication of Microfluidic Devices

In this Example, microfluidic devices including ten separate reaction wells were fabricated.

Specifically, devices were fabricated using soft lithography. Master templates were fabricated in SU-8 photoresist (Microchem) on silicon wafers using photolithography. Separate master templates were prepared for the chamber and channel layers of the device. The photoresist to form the ten reaction wells of the chamber layer was 300-μm high and 2-mm in diameter. The height of the photoresist to form the side channels and main channel of the channel layer was 50 μm and the width of the channel ranged from 150-260 μm. The devices were fabricated using polydimethylsiloxane (PDMS) to take advantage of the permeability of the polymer (for actuation of the sample solution) and the rapid prototyping capabilities. PDMS (Sylgard 184; Dow Corning) was mixed in a 1:10 ratio (base:cross linking agent), cast against the master templates to a height of ~1-mm, and cured at 65° C. overnight. The layer of PDMS forming the chamber layer was peeled away from the master and trimmed with a razor. Before use, ten different concentrations of antibiotic were pipetted (2.94 μL) into the 10 separate reaction wells and dried by evaporating the liquid. The layer of PDMS forming the channel layer was peeled away from the mold and trimmed with a razor. A 3-mm diameter vacuum hole and a 1-mm diameter inlet port were punched in the channel layer using tissue culture bores (Harris UniCore, Tedpella). The two PDMS layers (chamber and channel layers) were assembled by reversibly bonding the feature layers together. A plastic slip was placed on top of the channel layer to convert the vacuum hole into a vacuum well; the sole inlet port remained uncovered. The device was degassed at ~25 kPa in a vacuum for 30 min.

The resultant devices contained a single, main channel (50-μm tall, 150-μm wide) that connected the circular inlet port (1-mm diameter, ~1-mm deep, ~1.6 μL volume) located at one end and a circular vacuum well (3-mm diameter, ~1-mm deep, ~7.1 μL volume) located at the other end. When the chamber layer and channel layer were assembled, the ten reaction wells (2-mm diameter, 300-μm deep, 0.98 μL volume) were positioned along the length of the main channel. Each reaction well was connected to the main channel by a single straight side channel (3.2-mm long, 50-μm high, 260-μm wide).

Example 2

Loading and Degas-Driven Flow

In this Example, microfluidic devices prepared as described in Example 1 were used to demonstrate the loading and degas-driven flow in the microfluidic devices.

Specifically, various concentrations of blue dye were added into all ten reaction wells of the chamber layer of the device. After the liquid of the dye solution was evaporated, the device was assembled and vacuum degassed. The device was then removed from the vacuum and a 20-μL droplet of a solution of yellow dye was pipetted onto the inlet port. The movement of the yellow dye by degas-driven flow was then followed.

Figure 23:
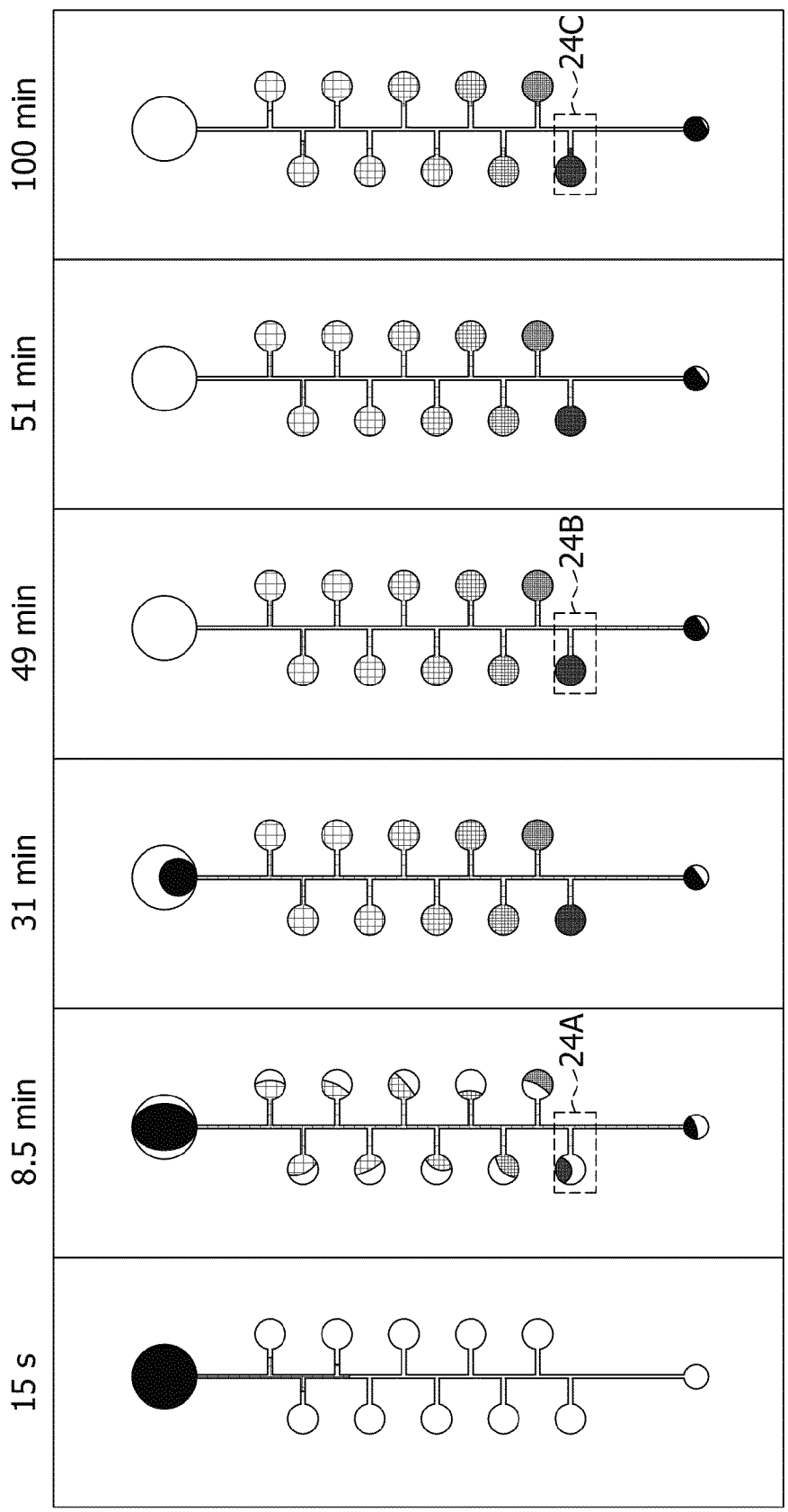
FIG. 23 is a translucent schematic illustration of a self-loading microfluidic device 100 showing the flow of a sample solution from 15 s to 100 min after the sample solution was added to the inlet port 206.
Figure 24A:
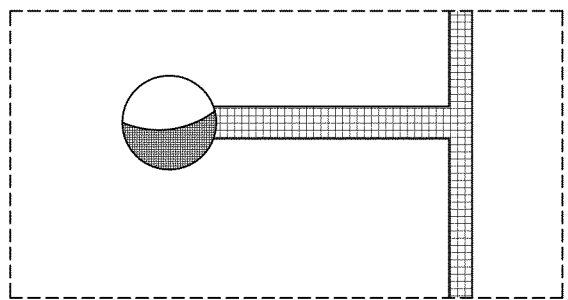
FIG. 24 is a translucent schematic illustration of (A) an enlargement of the boxed region shown at the 8.5 min time point of FIG. 23, (B) an enlargement of the boxed region shown at the 49 min time point of FIG. 23, and (C) an enlargement of the boxed region shown at the 100 min time point of FIG. 23.
Figure 24B:
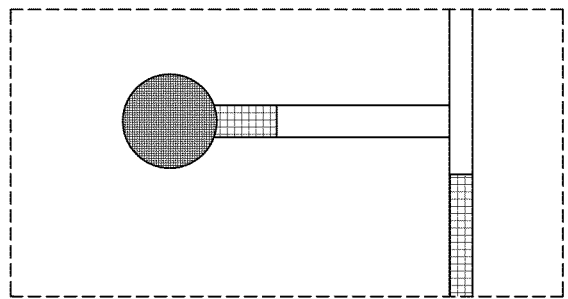
Figure 24C:
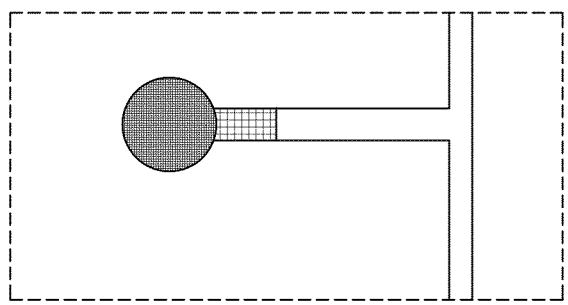

FIG. 23 is a sequence of illustrations depicting the loading and degas-driven flow of the yellow dye placed at the inlet port of the freshly degassed PDMS device. The yellow dye immediately filled the main channel and then filled the reaction wells by flowing through the side channel. The vacuum well continued to draw in the yellow dye until the droplet was consumed, at which point air was pulled into the device and traveled down the main channel isolating the yellow dye in the individual reaction wells. The boxes indicate three reaction wells of the device depicted in FIG. 24A-C. FIG. 24A demonstrates that the flow of yellow dye was unidirectional and prevented the outward diffusion of the content of the reaction chamber. FIG. 24B demonstrates that after each reaction well was filled with the yellow dye, the reaction well was isolated with air before an appreciable amount of dye diffused out of the reaction well. FIG. 24C demonstrates that after the yellow dye in each reaction well was isolated from each other, diffusion within the reaction well created a uniform distribution of dye.

Example 3

Controlling Concentration of Agents

In this Example, the reproducibility of controlling the concentration of agents in the reaction wells was determined.

Figure 25:
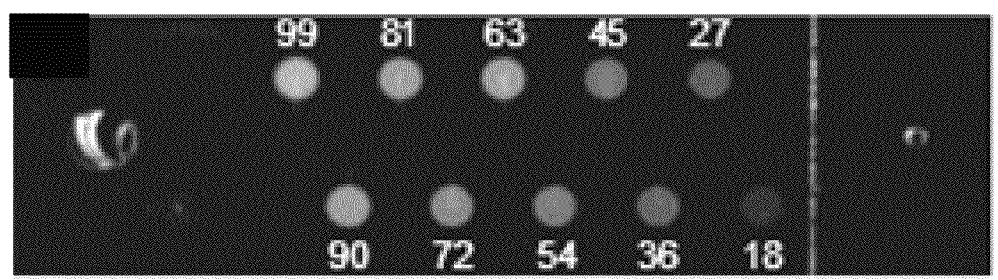
FIG. 25 is an image showing the fluorescence intensity of reconstituted fluorescein with deionized water in a self-loading microfluidic device 100 with various concentrations of fluorescein (18-99 μM) as described in Example 3.
Figure 26:
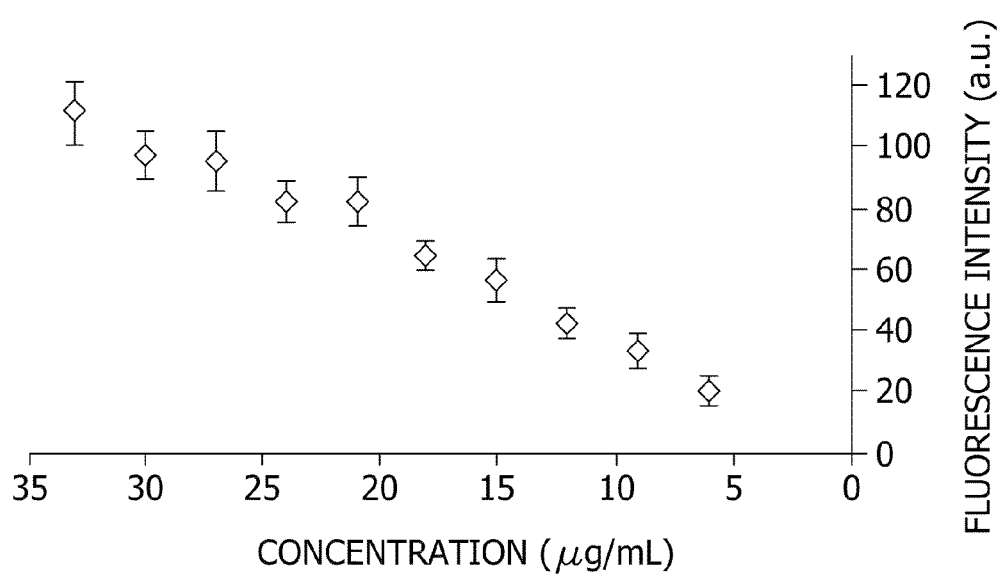
FIG. 26 is a graph illustrating the fluorescence intensity (a.u.) versus the concentration of fluorescent molecule added to reaction wells of a self-loading microfluidic device as described in Example 3.

Specifically, five devices were fabricated as described above and various concentrations of fluorescein (18-99 μM) were added to each reaction well and dried by evaporation. After the liquid was evaporated, the device was assembled and vacuum degassed. After degassing, a 20 μL droplet of deionized water was introduced at the inlet. After the liquid was introduced and isolated in the reaction wells to reconstitute the dried fluorescein, the fluorescence intensity of the reaction wells was imaged and quantified using ImageJ (FIG. 25). The mean fluorescence intensity of each chamber (n=5) between the five devices followed a linear trend (FIG. 26).

Example 4

Off-Chip Minimum Inhibitory Concentration Measurements

Off-chip MIC assays using the broth dilution method according to CLSI protocols were performed as control experiments and to validate experimental data obtained with the microfluidic device.

Specifically, antibiotic stock solutions (10 mg/mL) of vancomycin hydrochloride (MP Biomedicals), tetracycline hydrochloride (Eastman Kodak), and kanamycin monosulfate (Fisher BioReagents) were prepared in sterile deionized water. A 1:10 dilution series of the stock solutions in cation-adjusted Mueller-Hinton broth (CAMHB) was prepared and added to CAMBH (pH 7.3) to create a two-fold series dilution in which the total volume was 1 mL. Cell solutions of *E. faecalis* (1131), *P. mirabilis* (HI4320), *K. pneumoniae*, and *E. coli* (MG1655) were prepared in 13×100 mm tubes by adjusting the concentration of cells in overnight cultures to match the turbidity of a 0.5 McFarland standard (~108 CFU/mL) using CAMHB. The solutions were diluted 100-fold in CAMHB and 1 mL of the suspension was added to 1 mL of antibiotic solution—prepared as described above—to yield a final cell concentration of ~5×10$^5$ CFU/mL. The cultures were incubated for 20 h in a humidified incubator at 35° C. (no shaking) with the exception of experiments with vancomycin and *E. faecalis*, which were incubated for 24 h according to CLSI protocols. The MIC was determined as the lowest concentration of antibiotic at which no growth was visible after incubation.

MIC Measurements Using the Microfluidic Device

Minor adjustments were made to procedures mimicking the CLSI guidelines to perform MIC measurements using microfluidic devices prepared as described above. Antibiotic stock solutions (10 mg/mL in sterile deionized water) of vancomycin hydrochloride, tetracycline hydrochloride, and kanamycin monosulfate were used to prepare a 1:10 dilution series. Appropriate amounts of these dilutions were added to sterile deionized water to create a two-fold dilution series that varied from 0.5-1024 μg/mL. Antibiotic solution (2.94 μL) was added to each chamber with the lowest antibiotic concentration located closest to the inlet port and the highest antibiotic concentration located in the chamber closest to the vacuum well. After antibiotic loading, the device was placed in a laminar flow hood to evaporate the liquid. After the liquid was evaporated, the device was assembled by placing the layer of PDMS forming the channel section over the chamber layer containing the dried antibiotic such that the channels connected the chambers. The assembled device was then placed under vacuum.

Cell suspensions were prepared by adjusting the concentration of cells in overnight cultures to match the turbidity of a 0.5 McFarland standard (~108 CFU/mL) using CAMHB media, pH 7.3. The standardized culture was then diluted 1:200 in CAMBH media, pH 8.2 supplemented with 1% glucose and 0.05% phenol red to provide a colorimetric change upon growth. The device was removed from the vacuum and 20 μL of cell suspension was pipetted onto the inlet port. The device was incubated for 18 h at 35° C. in a humidified incubator. The MIC was determined as the lowest concentration of antibiotic in which bacteria did not grow. Bacterial growth changed the pH of the liquid nutrient media containing the indicator phenol red, and produced a visible color change that was used to identify the cell growth in chambers.

Figure 27:
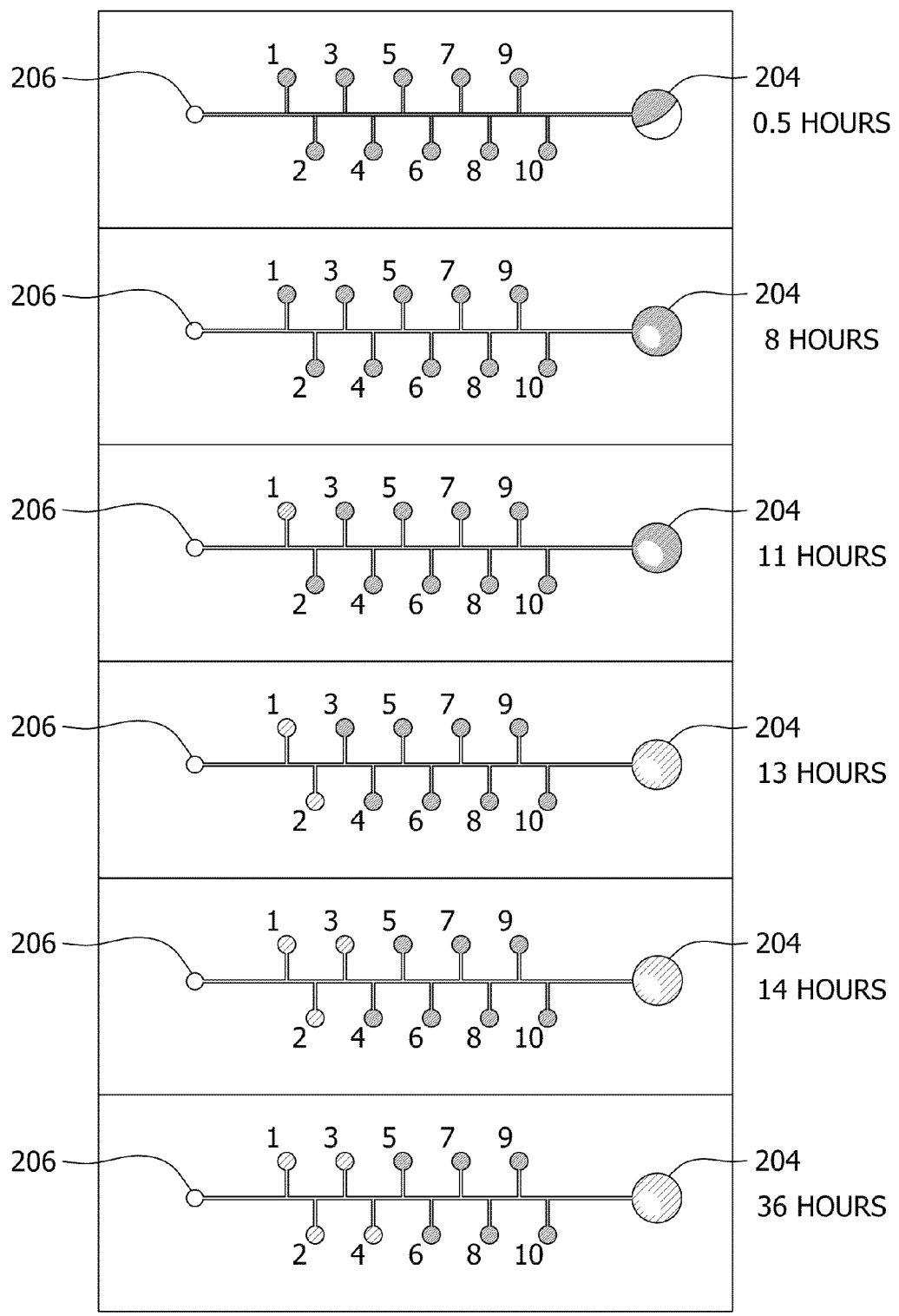
FIG. 27 is an illustration of the determination of the minimum inhibitory concentration of antibiotics to inhibit bacterial growth using self-loading microfluidic devices as described in Example 4.

FIG. 27 is an illustration showing that bacteria growth reached a level in the lowest antibiotic concentration by 11 hours, causing a pH change that was detected by a color change of the solution because of the pH indicator (wide hatched lines in chamber 1). At the endpoint of 36 hours, bacteria growth was observed in chambers 1-4, thus the minimum inhibitory concentration of the experiment was the amount in chamber 5. Therefore, chamber 5 represents the lowest concentration at which there was no growth and the chamber appeared red because of the pH indicator.

Comparison of MIC of Bacteria to Different Antibiotics

MIC measurements obtained using the microfluidic devices were compared to the control broth dilution technique.

Specifically, bacterial species were chosen to include Gram-positive (*E. faecalis* (1131)) and Gram-negative (*E. coli* (MG1655), *P. mirabilis* (HI4320), and *K. pneumoniae*) organisms from four different clinically relevant families. Three different classes of antibiotics that inhibit different targets and have activity against Gram-negative and Gram-positive bacteria were chosen. Vancomycin inhibits the maturation of the peptidoglycan layer of the cell wall during growth, and is specific for treating Gram-positive bacteria. Tetracycline is a broad-spectrum antibiotic that inhibits protein synthesis via binding to the 30S subunit of the ribosome. Kanamycin is a relatively broad-spectrum antibiotic that binds the 30S subunit of the ribosome and causes the mistranslation of proteins.

Results of the MIC measurements using the microfluidic device closely matched those performed using the broth dilution method (Table 1). The MIC values determined using the microfluidic device were all within a two-fold dilution of the MIC values determined using the broth dilution method, which is an acceptable discrepancy when comparing assay results according to the CLSI.

TABLE 1

MIC measurement.

| Species | Vanomycin | | Tetracycline | | Kanamycin | |
| --- | --- | --- | --- | --- | --- | --- |
| | Device | Broth | Device | Broth | Device | Broth |
| E. faecalis | 8 | 4 | 64 | 32 | 128 | 64 |
| P. mirabilis | >1024 | >1024 | 128 | 256 | 8 | 4 |
| K. pneumoniae | >1024 | >1024 | 8 | 8 | 2 | 2 |
| E. coli | 512 | 256 | 2 | 1 | 4 | 8 |

Example 5

Isolating Kanamycin-Resistant *E. coli* Mutants

In this Example, kanamycin-resistant *E. coli* were isolated from wild type bacteria to determine whether the microfluidic device could detect increased antibiotic resistance.

Specifically, 100 μL of an overnight culture of *E. coli* MG1655 were plated on LB agar plates supplemented with 16 μg/mL kanamycin; the antibiotic concentration was ~2× the MIC of kanamycin measured against *E. coli* MG1655. After overnight incubation at 35° C., 24 colonies were identified that grew in the presence of 16 μg/mL kanamycin. One of these colonies was characterized for its sensitivity to kanamycin in the microfluidic device. The kanamycin-resistant strain was compared to the wild type parent strain.

A range of concentrations of kanamycin (final concentration 2-1024 μg/mL) were added to the reaction wells of two devices and evaporated. The devices were assembled and placed under vacuum for degassing. After the devices were removed from the vacuum, an aliquot (20 μL) of a suspension of cells of the resistant strain was introduced into the inlet port of one device and an aliquot (20 μL) of a suspension of cells of the wild type strain was introduced into the inlet port of the second device. Degas-driven flow filled and isolated the samples in the chambers. The devices were incubated for 18 h at 35° C. in a humidified incubator.

To eliminate external equipment needed for interpreting the test results, a pH sensor was incorporated to indicate cell growth. Specifically, the pH indicator phenol red (0.05% w/v) and glucose (1% w/v) were added to CAMHB media and adjusted the pH to 8.2. Phenol red was selected as it produces a distinct color change close to neutral pH and is not absorbed by PDMS. At the initial pH of the nutrient media, pH 8.2, phenol red appears bright red. The metabolism of glucose (or other sugars) by bacteria produces organic acids and decreases the pH of nutrient media. The pH change (pH<6.8) in the reaction wells of the devices in which bacteria grew made the phenol red in the nutrient media appear bright yellow.

A change in color was only observed in chambers in which bacteria grew. Thus, the MIC of the kanamycin-resistant *E. coli* strain and the susceptible strain was determinable by visually identifying the chamber containing the lowest concentration of kanamycin in which the pH indicator remained red. The MIC of the resistant strain was determined to be 64 μg/mL and the MIC of the wild type strain was determined to be 4 μg/mL. The MIC for the resistant strain and the wild type strain in control experiments using standard liquid broth dilution assays was determined to be 128 μg/mL for the resistant strain and 8 μg/mL for the wild type strain. These results were within the ±1 two-fold dilution discrepancy that is considered acceptable by the CLSI.

Example 6

Determining Bacterial Antibiotic Susceptibility to Multiple Antibiotics Using a Single Microfluidic Device In this Example, a single microfluidic device was used to simultaneously test the susceptibility of the kanamycin-resistant strain of *E. coli* MG1655 described above to multiple antibiotics using breakpoint values.

In clinical microbiology, a strain is classified as susceptible, intermediate, or resistant based on the relationship of the MIC of an antibiotic to specified 'breakpoint' values. Breakpoint values are set by organizations, such as the CLSI, and take into consideration MIC values of wild type strains, pharmacokinetic/pharmacodynamic data, and clinical outcomes. Breakpoint values are available for specific clinically relevant pairings of bacterial species and antibiotics and enable clinical decisions without knowing the exact MIC value.

Specifically, vancomycin, tetracycline, and kanamycin were added to the reaction wells of a single device. The most common breakpoints for vancomycin (susceptible≤2 μg/mL, resistant>2 μg/mL), tetracycline (susceptible≤1 μg/mL, intermediate=2 μg/mL, resistant>2 μg/mL), and gentamicin (susceptible≤2 μg/mL, intermediate=4 μg/mL, resistant>4 μg/mL) were used. As there are no published breakpoints available for kanamycin, the breakpoint values for the structurally related aminoglycoside, gentamicin, against aerobic bacteria was used. A microfluidic device with ten chambers was prepared as described in Example 1 above. The ten chambers were divided into three chambers for each antibiotic vancomycin (2, 4, 8 μg/mL), tetracycline (0.5, 1, 2 μg/mL), and kanamycin (1, 2, 4 μg/mL) and one chamber for a control containing no antibiotic. After loading and incubation (18 h), growth was observed in the control chamber and at all concentrations of kanamycin and vancomycin. The bacterial strain grew at the lowest two concentrations of tetracycline but not at the highest concentration. Thus, tetracycline inhibited the growth of this strain, whereas vancomycin and kanamycin did not have any effect. Based on these results, the phenotype of the kanamycin-resistant strain of *E. coli* MG1655 was concluded to be vancomycin resistant (as to be expected for all Gram-negative bacteria), tetracycline intermediate, and kanamycin resistant. These results demonstrate that the microfluidic device can be used to perform critical assays in a clinical setting to aid in the prescription of effective antibiotics to treat infections.

Example 7

Microbe Identification

In this Example, self-loading microfluidic devices were used to identify bacterial species.

Figure 28:
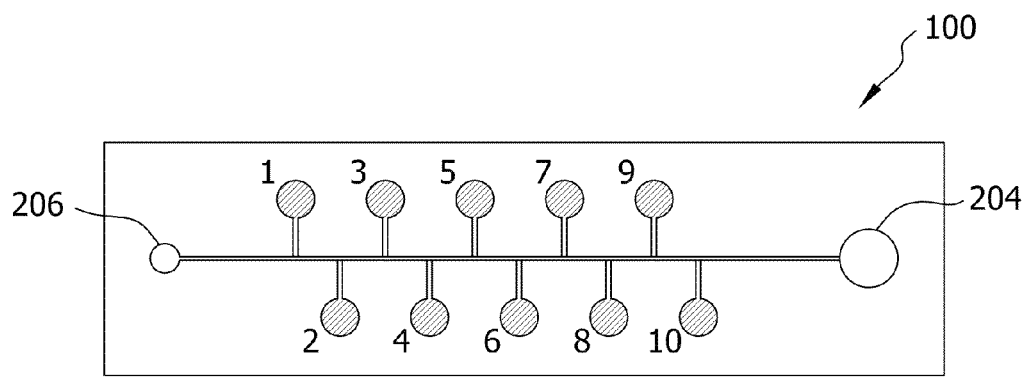
FIG. 28 is a translucent schematic illustration showing reaction wells with various sugar solutions including (1) cellbiose, (2) glycerol, (3) lactose, (4) mannitol, (5) mannose, (6) raffinose, (7) sucrose, (8) trehalose, (9) xylose, and (10) control (no sugar) as described in Example 7.

Self-loading microfluidic devices were prepared as described above. Reaction wells were filled with different sugar solutions including (1) cellbiose, (2) glycerol, (3) lactose, (4) mannitol, (5) mannose, (6) raffinose, (7) sucrose, (8) trehalose, (9) xylose, and (10) control (no sugar) (FIG. 28). The final concentration of the sugar in each chamber was 1% (w/v). After loading the sugar solutions, the liquid was evaporated as described above. The devices were then assembled and degassed by vacuum.

Cultures of *A. baumannii*-1, *A. baumannii*-2, *K. pneumoniea*-1, *K. pneumoniea*-2, *S. aureus*-1, *S. aureus*-2, *E. coli* (UT189), *E. faecalis*-1, *E. faecalis*-2, *V. cholerae*-1, and (11) *V. cholerae*-2 were grown for 15 hours in LB (pH 7.0). The cultures were then diluted at a ratio of 1:50 in LB containing 0.05% (w/v) phenol red (pH8.2) and added to individual devices using degas-driven flow. Growth of bacteria results in a pH change of the LB that causes a color change from red (illustrated in FIGS. 29 and 30 as filled chambers) to yellow (illustrated in FIGS. 29 and 30 as hatched chambers).

Results observed in microfluidic devices are illustrated in FIGS. 29A-F and 30A-E. The predicted growth as compared to devices and culture tubes are summarized in Table 2.

As illustrated in FIGS. 29A and 29B, *A. baumannii*-1 and *A. baumannii*-2 grew in the chambers containing mannose (chamber 5) and xylose (chamber 9) by 8 hours of incubation. *A. baumannii*-1 and *A. baumannii*-2 in xylose did not grow in culture tubes (Table 2). In most cases, detection of bacteria was more rapid in devices than in culture tubes.

As illustrated in FIGS. 29C and 29D, *K. pneumoniea*-1 and *K. pneumoniea*-2 grew in glycerol (chamber 2), mannitol (chamber 4), raffinose (chamber 6), sucrose (chamber 7), and trehalose (chamber 8) by 4 hours of incubation in the devices. Differences between cultures grown in devices and culture tubes were observed in the cellbiose, mannose, and xylose conditions (Table 2).

As illustrated in FIG. 29E, *S. aureus*-1 grew in glycerol (chamber 2), mannitol (chamber 4), mannose (chamber 5), sucrose (chamber 7), and trehalose (chamber 8) by 8 hours of incubation in the devices. *S. aureus*-2 growth was observed in these same sugars by 18 hours of incubation in devices (FIG. 29F). As summarized in Table 2, growth of *S. aureus* in glycerol was predicted and observed in the device, but no growth was observed using the culture tube method. Without being bound by theory, it may be possible that the different results observed for the device versus the culture tube is due to an acceleration of growth in the smaller volume of LB in the device. This result may also be enhanced by the increased surface-to-volume ratio of the reaction wells as compared to the culture tubes. Additionally, the effect may be enhanced by the gas permeability of the PDMS layers. As summarized in Table 2, growth was predicted for the lactose condition and was observed in culture tubes, but growth was not observed in devices incubated for 8 hours or 18 hours (chamber 3). The absence of color change may be that it changed and then changed back before devices were analyzed for color change.

Figure 30A:
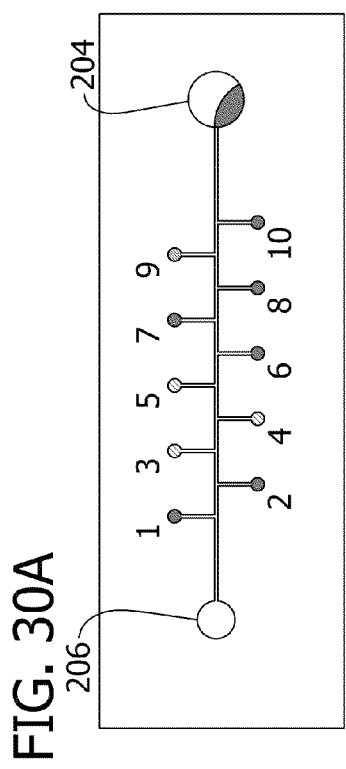
FIG. 30A-E is a translucent schematic illustration of the results showing bacterial identification using self-loading microfluidic devices as described in Example 7.
Figure 30C:
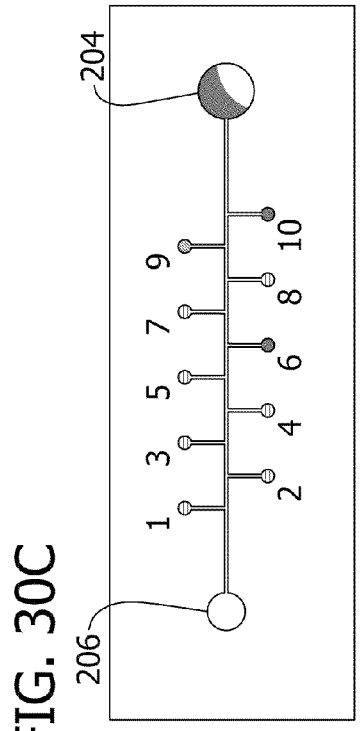

As illustrated in FIG. 30A, *E. coli* (UT189)-1 grew in lactose (chamber 3), mannitol (chamber 4), mannose (chamber 5), and xylose (chamber 9). As illustrated in FIGS. 30B and 30C, *E. faecalis*-1 and *E. faecalis*-2 grew in cellbiose (chamber 1), glycerol (chamber 2), lactose (chamber 3), mannitol (chamber 4), mannose (chamber 5), sucrose (chamber 7), and trehalose (chamber 8) by 18 hours of incubation. These results correlated with both the predicted growth and the observed growth in culture tubes (Table 2).

Figure 30E:
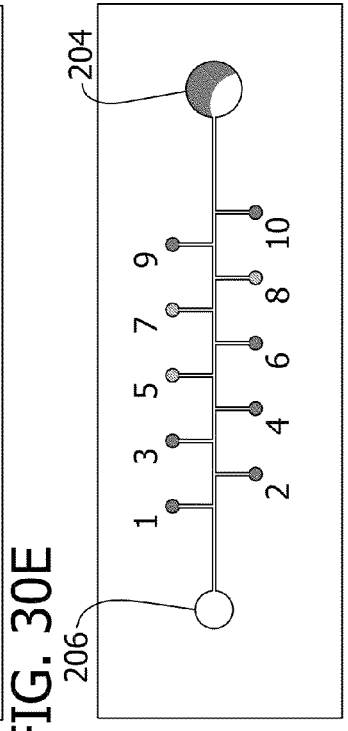
Figure 30B:
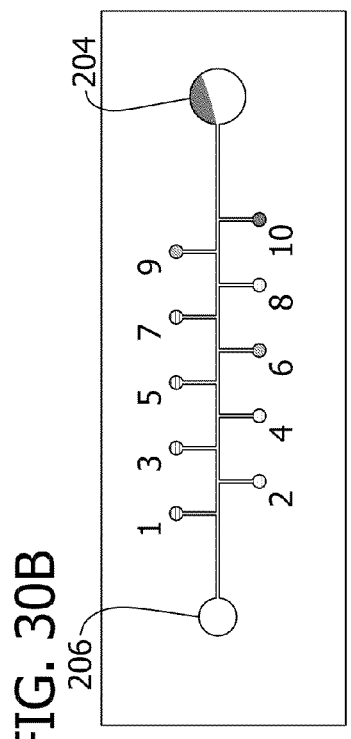
Figure 30D:
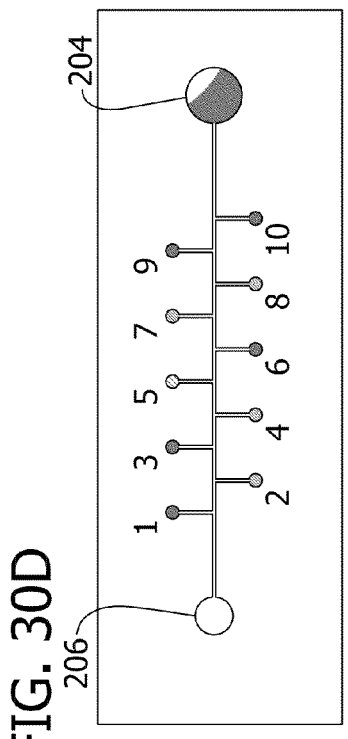

As illustrated in FIGS. 30D and 30E, *V. cholerae*-1 and *V. cholerae*-2 grew in mannose (chamber 5), sucrose (chamber 7), and trehalose (chamber 8) by 4 hours of incubation.

TABLE 2

Summary of Growth in Various Sugars.

| Sugar | E. faecalis | | | S. aureus | | | K. pneumoniae | | | A. baumannii | | | E. coli (UT189) | | |
|---|---|---|---|---|---|---|---|---|---|---|---|---|---|---|---|
| | Predicted | Device | Tube | Predicted | Device | Tube | Predicted | Device | Tube | Predicted | Device | Tube | Predicted | Device | Tube |
| Cellbiose | + | + | + | − | − | − | N/A | − | + | N/A | − | − | − | − | − |
| Glycerol | + | + | + | + | + | − | N/A | + | + | N/A | − | − | + | − | − |
| Lactose | + | + | + | + | − | + | N/A | − | − | N/A | − | − | + | + | + |
| Mannitol | + | + | + | + | + | + | N/A | + | + | N/A | − | − | + | + | + |
| Mannose | + | + | + | + | + | + | N/A | − | + | N/A | + | + | N/A | − | + |
| Raffinose | − | − | − | − | − | − | N/A | + | + | N/A | − | − | − | − | − |
| Sucrose | + | + | + | + | + | + | N/A | + | + | N/A | − | − | − | − | − |
| Trehalose | + | + | + | + | + | + | N/A | + | + | N/A | − | − | + | − | + |
| Xylose | − | − | − | − | − | − | N/A | − | + | N/A | + | − | + | − | + |

+ indicates growth
− indicates no growth

The experiments described above demonstrate that that the self-loading microfluidic device may be used in a variety of chemical and biological assays such as, for example, performing chemical reactions and identifying organisms by incorporating agents in the reaction wells. The self-loading microfluidic devices may be manufactured and supplied as a fully assembled, degassed and vacuum packaged unit including an agent for point-of-care applications. The self-loading microfluidic device may alternatively be manufactured and supplied without pre-loading an agent to allow for customized agents and/or assays to be performed using the self-loading microfluidic device.

In view of the above, it will be seen that the several advantages of the disclosure are achieved and other advantageous results attained. As various changes could be made in the above devices and methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of performing an assay, the method comprising:
    adding an agent in liquid form to a reaction well of a self-loading microfluidic device, wherein the self-loading microfluidic device further comprises a porous organic polymer and an inlet port, a vacuum well, a main channel, and a side channel;
    drying the liquid to form a dried agent;
    degassing the self-loading microfluidic device in a low pressure environment;
    removing the degassed self-loading microfluidic device from the low pressure environment;
    adding a sample solution to the inlet port;
    flowing the sample solution from the inlet port to fill the reaction well by degas-driven flow;
    incubating the self-loading microfluidic device; and
    analyzing the reaction well.

2. The method of claim 1, wherein the assay is a chemical assay, a biological assay, and combinations thereof.

3. The method of claim 2, wherein the assay is selected from the group consisting of determining a minimum inhibitory concentration of an antibiotic, determining a therapeutically effective amount of a drug, determining an effect of a drug on a cell, determining an effect of a drug candidate on a cell, identifying an organism, determining a biological profile of an analyte, determining an antibody-antigen interaction, determining an identity of an analyte, amplification of a nucleic acid, and detection of a nucleic acid, and combinations thereof.

4. The method of claim 3, wherein the amplification is an isothermic amplification assay.

5. The method of claim 3, wherein the organism is selected from the group consisting of a multicellular organism, a cell, a virus, a bacterium, a fungus, and a spore.

* * * * *